(12) United States Patent
Borden et al.

(10) Patent No.: US 7,879,109 B2
(45) Date of Patent: Feb. 1, 2011

(54) CONTINUOUS PHASE COMPOSITE FOR MUSCULOSKELETAL REPAIR

(75) Inventors: Mark D Borden, Foothill Ranch, CA (US); Joseph M Hernandez, Torrance, CA (US); Edwin C Shors, Laguna Beach, CA (US)

(73) Assignee: Biomet Manufacturing Corp., Warsaw, IN (US)

( * ) Notice: Subject to any disclaimer, the term of this patent is extended or adjusted under 35 U.S.C. 154(b) by 1260 days.

(21) Appl. No.: 11/008,075

(22) Filed: Dec. 9, 2004

(65) Prior Publication Data

US 2006/0121084 A1 Jun. 8, 2006

Related U.S. Application Data

(60) Provisional application No. 60/634,448, filed on Dec. 8, 2004.

(51) Int. Cl.
*A61F 2/02* (2006.01)
(52) U.S. Cl. .................................................. 623/23.76
(58) Field of Classification Search ... 623/17.11–17.16, 623/23.56–23.63
See application file for complete search history.

(56) References Cited

U.S. PATENT DOCUMENTS

| | | |
|---|---|---|
| 4,349,921 A | 9/1982 | Kuntz |
| 4,421,112 A | 12/1983 | Mains et al. |
| 4,450,591 A | 5/1984 | Rappaport |
| 4,516,276 A | 5/1985 | Mittelmeier et al. |
| 4,612,923 A | 9/1986 | Kronenthal |
| 4,655,777 A | 4/1987 | Dunn et al. |
| 4,678,470 A | 7/1987 | Nashef et al. |
| 4,713,076 A | 12/1987 | Draenert |
| 4,743,256 A | 5/1988 | Brantigan |
| 4,770,860 A | 9/1988 | Ewers et al. |
| 4,834,754 A | 5/1989 | Shearing |
| 4,842,603 A | 6/1989 | Draenert et al. |
| 4,863,472 A | 9/1989 | Törmälä et al. |
| 4,878,915 A | 11/1989 | Brantigan |
| 4,904,261 A | 2/1990 | Dove et al. |
| 4,976,736 A | 12/1990 | White et al. |
| 5,015,255 A | 5/1991 | Kuslich |
| 5,026,373 A | 6/1991 | Ray et al. |
| 5,053,039 A | 10/1991 | Hofmann et al. |
| 5,059,209 A | 10/1991 | Jones |
| 5,192,327 A | 3/1993 | Brantigan |

(Continued)

FOREIGN PATENT DOCUMENTS

WO   WO 97/46178    12/1997

(Continued)

OTHER PUBLICATIONS

Agrawal et al., "Technique to Control pH in Vicinity of Biodegrading PLA-PGA Implants", John Wiley & Sons, Inc. (1997) pp. 105-114.

(Continued)

*Primary Examiner*—Anu Ramana
(74) *Attorney, Agent, or Firm*—Harness, Dickey

(57) ABSTRACT

A composite material for positioning in the anatomy to form a selected function therein. The composite may be resorbable over a selected period of time. The composite may allow for selected bone ingrowth as absorption of the composite occurs.

8 Claims, 15 Drawing Sheets

U.S. PATENT DOCUMENTS

| | | | |
|---|---|---|---|
| 5,306,309 A | 4/1994 | Wagner et al. | |
| 5,338,772 A | 8/1994 | Bauer et al. | |
| 5,360,450 A | 11/1994 | Giannini | |
| 5,425,772 A | 6/1995 | Brantigan | |
| 5,433,751 A | 7/1995 | Christel et al. | |
| 5,484,437 A | 1/1996 | Michelson | |
| 5,522,817 A | 6/1996 | Sander et al. | |
| 5,529,075 A | 6/1996 | Clark | |
| 5,601,565 A | 2/1997 | Huebner | |
| 5,607,424 A | 3/1997 | Tropiano | |
| 5,609,635 A | 3/1997 | Michelson | |
| 5,626,861 A | 5/1997 | Laurencin et al. | |
| 5,645,596 A | 7/1997 | Kim et al. | |
| 5,650,108 A | 7/1997 | Nies et al. | |
| 5,669,909 A | 9/1997 | Zdeblick et al. | |
| 5,702,449 A | 12/1997 | McKay | |
| 5,722,978 A | 3/1998 | Jenkins, Jr. et al. | |
| 5,728,159 A | 3/1998 | Stroever et al. | |
| 5,766,251 A | 6/1998 | Koshino | |
| 5,766,618 A | 6/1998 | Laurencin et al. | |
| 5,776,199 A | 7/1998 | Michelson | |
| 5,865,845 A | 2/1999 | Thalgott | |
| 5,895,426 A | 4/1999 | Scarborough et al. | |
| 5,899,939 A | 5/1999 | Boyce et al. | |
| 5,984,967 A | 11/1999 | Zdeblick et al. | |
| 5,989,289 A | 11/1999 | Coates et al. | |
| 6,008,433 A | 12/1999 | Stone | |
| 6,039,762 A | 3/2000 | McKay | |
| 6,077,989 A | 6/2000 | Kandel et al. | |
| 6,086,593 A | 7/2000 | Bonutti | |
| 6,099,531 A | 8/2000 | Bonutti | |
| 6,102,950 A | 8/2000 | Vaccaro | |
| 6,136,032 A | 10/2000 | Viladot Perice et al. | |
| 6,139,585 A | 10/2000 | Li | |
| 6,143,033 A | 11/2000 | Paul et al. | |
| 6,165,203 A | 12/2000 | Krebs | |
| 6,187,047 B1 | 2/2001 | Kwan et al. | |
| 6,203,574 B1 | 3/2001 | Kawamura | |
| 6,227,149 B1 | 5/2001 | Host et al. | |
| 6,241,771 B1 | 6/2001 | Gresser et al. | |
| 6,277,149 B1 | 8/2001 | Boyle et al. | |
| 6,281,257 B1 | 8/2001 | Ma et al. | |
| 6,283,997 B1 | 9/2001 | Garg et al. | |
| 6,296,667 B1 | 10/2001 | Johnson et al. | |
| 6,323,146 B1 | 11/2001 | Pugh et al. | |
| 6,331,312 B1 | 12/2001 | Lee et al. | |
| 6,332,779 B1 | 12/2001 | Boyce et al. | |
| 6,333,029 B1 | 12/2001 | Vyakarnam et al. | |
| 6,340,648 B1 | 1/2002 | Imura et al. | |
| 6,371,988 B1 | 4/2002 | Pafford et al. | |
| 6,376,573 B1 | 4/2002 | White et al. | |
| 6,391,031 B1 | 5/2002 | Toomey | |
| 6,406,498 B1 | 6/2002 | Törmälä et al. | |
| 6,432,106 B1 | 8/2002 | Fraser | |
| 6,447,544 B1 | 9/2002 | Michelson | |
| 6,458,162 B1 | 10/2002 | Koblish et al. | |
| 6,503,278 B1 | 1/2003 | Pohjonen et al. | |
| 6,503,279 B1 | 1/2003 | Webb et al. | |
| 6,524,345 B1 | 2/2003 | Valimaa et al. | |
| 6,527,810 B2 | 3/2003 | Johnson et al. | |
| 6,530,955 B2 | 3/2003 | Boyle et al. | |
| D472,972 S | 4/2003 | Anderson | |
| 6,575,982 B1 | 6/2003 | Bonutti | |
| 6,595,998 B2 * | 7/2003 | Johnson et al. | 606/90 |
| 6,616,698 B2 | 9/2003 | Scarborough | |
| 6,673,075 B2 | 1/2004 | Santilli | |
| 6,676,703 B2 | 1/2004 | Biscup | |
| 6,686,437 B2 | 2/2004 | Buchman et al. | |
| 6,696,073 B2 | 2/2004 | Boyce et al. | |
| 6,702,821 B2 | 3/2004 | Bonutti | |
| 6,716,245 B2 | 4/2004 | Pasquet et al. | |
| 6,726,722 B2 | 4/2004 | Walkenhorst et al. | |
| 6,731,988 B1 | 5/2004 | Green | |
| 6,733,535 B2 | 5/2004 | Michelson | |
| 6,736,849 B2 | 5/2004 | Li et al. | |
| 6,749,636 B2 | 6/2004 | Michelson | |
| 6,761,739 B2 | 7/2004 | Shepard | |
| 6,770,078 B2 | 8/2004 | Bonutti | |
| D497,993 S | 11/2004 | Dixon et al. | |
| 6,840,961 B2 * | 1/2005 | Tofighi et al. | 623/23.61 |
| 6,843,807 B1 | 1/2005 | Boyce et al. | |
| 6,863,899 B2 | 3/2005 | Koblish et al. | |
| 6,916,321 B2 | 7/2005 | TenHuisen et al. | |
| 6,921,402 B2 | 7/2005 | Contiliano et al. | |
| 2002/0037799 A1 | 3/2002 | Li et al. | |
| 2002/0169066 A1 | 11/2002 | Cassidy et al. | |
| 2003/0144743 A1 | 7/2003 | Edwards et al. | |
| 2003/0167093 A1 | 9/2003 | Xu et al. | |
| 2003/0233147 A1 | 12/2003 | Nicholson et al. | |
| 2004/0002770 A1 | 1/2004 | King et al. | |
| 2004/0093089 A1 | 5/2004 | Ralph et al. | |
| 2004/0115172 A1 | 6/2004 | Bianchi et al. | |
| 2004/0243242 A1 | 12/2004 | Sybert et al. | |
| 2005/0070905 A1 | 3/2005 | Donnelly et al. | |

FOREIGN PATENT DOCUMENTS

| | | |
|---|---|---|
| WO | WO 97/47334 | 12/1997 |
| WO | WO 2006/015316 | 2/2006 |

OTHER PUBLICATIONS

Ara et al., Effect of blending calcium compounds on hydrolytic degradation of poly (DL-lactic acid-co-glycolic acid), Biomaterials 23 (2002) pp. 2479-2483.

Borden et al., "Structural and human cellular assessment of a novel microsphere-based tissue engineered scaffold for bone repair", Biomaterials 24 (2004) pp. 597-609.

Borden et al., "Tissue engineered microsphere-based matrices for bone repair: design and evaluation", Biomaterials 23 (2002) pp. 551-559.

Borden, et al. "The sintered microsphere matrix for bone tissue engineering: In vitro osteoconductivity studies", © 2002 Wiley Periodicals, Inc. (pp. 421-429).

Böstman, "Clinical biocompatibility of biodegradable orthopaedic implants for internal fixation: a review", Biomaterials 21 (2000) pp. 2616-2621.

Böstman, M.D., Ph.D et al., "Adverse Tissue Reactions to Bioabsorbable Fixation Devices", Clinical Orthopaedics and Related Research 371 (Feb. 2000) pp. 216-227.

Chu et al., "Scanning electron microscopic study of the hydrolytic degradation of poly(glycolic acid) suture", Journal of Biomedical Materials Research, vol. 16, (1982) pp. 417-430.

Chu, "The in-vitro degradation of poly(glycolic acid) sutures—effect of pH", Journal of Biomedical Materials Research, V.15 (1981) pp. 795-804.

Gautier et al., "Poly (α-hydroxyacids) for application in the spinal cord: Resorbability and biocompatibility with adult rat Schwann cells and spinal cord", (1998) pp. 642-654.

Koskikare et al., "Fixation of ostotomies of the distal femur with absorbable, self-reinforced, poly-L-lactide plates" "An experimental study on rabbits", Arch Orthop Trauma Surg 116 (1997) pp. 352-356.

Leenslag et al., "Resorbable materials of poly (L-lactide). VI. Plates and screws for internal fracture fixation", Biomaterials vol. 8 (Jan. 1987) pp. 70-73.

Mäkelä et al., "Healing of Physeal Fracture after Fixation with Biodegradable Self-Reinforced Polyglycolic Acid Pins. An Experimental Study on Growing Rabbits", Clinical Materials, pp. 1-12.

Rovinsky, M.D. et al., Case Report, "Osteolytic Reaction to Polylevolactic Acid Fracture Fixation", www.orthobluejournal.com, vol. 24, No. 2 (Feb. 2001) pp. 177-179.

Taylor et al., "Six Bioabsorbable Polymers: In Vitro Acute Toxicity of Accumulated Degradation Products", Journal of Applied Biomaterials, vol. 5, pp. (1994) 151-157.

Tencer et al. "Mechanical and bone ingrowth properties of a polymer-coated, porous, synthetic, coralline hydroxyapatite bone-graft material", Annals of the New York Academy of Sciences 1988 United States, vol. 523, 1988, pp. 157-172, XP009060816 ISSN: 0077-8923 "Introduction" and "Summary".

Tencer et al., "Bone Ingrowth into Polymer Coated Porous Synthetic Coralline Hydroxyapatite", IEEE/Engineering in Medicine and Biology Society Annual Conference 8th. 1986 IEEE, New York, NY, USA, 1986, pp. 1668-1671, XP009060826 abstract.

Törmälä et al., "Ultra-high-strength absorbable self-reinforced polyglycolide (SR-PGA) composite rods for internal fixation of bone fractures: In vitro and in vivo study", Journal of Biomedical Materials Research, vol. 25 (1991) 1-22.

Tuompo et al., "Comparison of polylactide screw and expansion bolt in bioabsorbable fixation with patellar tendon bone graft for anterior cruciate ligament rupture of the knee", Knee Surg, Sports Traumatol, Arthrosc (1999) pp. 296-302.

Vainionpää et al., "Strength and strength retention in vitro, of absorbable, self-reinforced polyglycolide (PGA) rods for fracture fixation", Biomaterials, vol. 8 (Jan. 1987) pp. 46-48.

University of Nebraska Lincoln, "Polymerization of Lactide and Glycolide Using Solid State Initiator," Dr. Dipanjan Nag.

Myerson, Mark S., M.D., "The Use of Osteotomy to Correct Foot and Ankle Deformities", Foot and Ankle Disorders, 2000, vol. 2 Chapter 41, pp. 999-1016.

Vanore, John V. et al., "Diagnosis and Treatment of First Metatarsophalengeal Joint Disorders. Section 1: Hallux Valgus", May/Jun. 2003. The Journal of Foot & Ankle Surgery, vol. 42, No. 3, pp. 112-123.

Vanore, John V. et al., "Diagnosis and Treatment of First Metetarsophalengeal Joint Disorders. Section 2: Hallux Valgus", May/Jun. 2003. The Journal of Foot & Ankle Surgery, Vol. 42, No. 3, pp. 124-136.

Tencer, A. F. et al. "Compressive Properties of Polymer Coated Synthetic Hydroxyapatite for Bone Grafting" Jounral of Biomedical Materials Research, vol. 19, 957-969 (1985).

* cited by examiner

CONTINUOUS PHASE COMPOSITE FOR MUSCULOSKELETAL REPAIR

CROSS-REFERENCE TO RELATED APPLICATIONS

This application claims the benefit of U.S. Provisional Application No. 60/634,448, filed on Dec. 8, 2004. The disclosure of the above application is incorporated herein by reference.

BACKGROUND

The present teachings relate generally to materials useful in orthopaedic surgery, including orthopaedic implants composed of resorbable materials.

In general, the human musculoskeletal system is composed of a variety of tissues including bone, ligaments, cartilage, muscle, and tendons. Tissue damage or deformity stemming from trauma, pathological degeneration, or congenital conditions often necessitates surgical intervention to restore function. During these procedures, surgeons can use orthopaedic implants to restore function to the site and facilitate the natural healing process.

Current orthopaedic implants are generally composed of non-reasonable metals, ceramics, polymers, and composites. However, in some instances, it may be desirable to have an implant made of resorbable material. These bioresorbable or biodegradable materials are characterized by the ability to be chemically broken down into harmless by-products that are metabolized or excreted by the body. Materials of this type can offer an advantage over conventional non-resorbable implant materials. Bioresorbable implants provide their required function until the tissue is healed, and once their role is complete, the implant is resorbed by the body. The end result is healthy tissue with no signs that an implant was ever present.

Bioresorbable materials are substances well known in the art. This includes resorbable polymers such as poly(lactic acid) [PLA] and poly(glycolic acid) [PGA], and ceramics such as hydroxyapatite, tricalcium phosphate, and calcium carbonate. Additionally, polymer/ceramic composites have also been used as an implant material. Overall, these materials have been used to fabricate a large range of orthopaedic implants including screws, plates, pins, rods, spacers, and the like. Clinically, these devices have a long history of use that spans a wide variety of surgical procedures. Resorbable devices have been used in applications such as fracture fixation, bone grafting, spinal fusion, soft tissue repair, and deformity correction.

SUMMARY

A composite material for positioning in the anatomy to perform a selected function therein is disclosed. The composite may be resorbable over a selected period of time. The composite may allow for selected bone ingrowth as absorption of the composite occurs. Also, the composite may include a first material of a first resorption profile and a second material of a second resorption profile.

According to various embodiments an implantable resorbable material is disclosed. The material can include a first material operable to be resorbed into an anatomy at a first resorption rate and defining a plurality of pores. A second material operable to be resorbed into the anatomy at a second resorption rate can be positioned relative to the first material to substantially fill at least a sub-plurality of the plurality of the pores. The first resorption rate of the first material can be different than the second resorption rate of the second material.

According to various embodiments a method of forming a resorbable implant is disclosed. The method can include selecting a first material including a first resorption rate and selecting a second material having a second resorption rate. A porous structure of the first material can be provided and a composite can be formed with the first material and the second material. The composite can be formed by substantially filling at least a sub-plurality of the plurality of the pores with the second material. An implant can be formed of the composite. The resorption rate of the first material is different than the resorption rate of the second material to allow a bone ingrowth after implantation of the implant.

According to various embodiments a method of forming a resorbable implant is disclosed. The method may include selecting a region of the anatomy to position an implant. In the region of the anatomy selected a force produced, a bone regrowth rate, a length of time that the implant should retain a selected strength, or other properties can be determined. A resorption rate of at least a portion of the implant after implantation can also be determined. A first material can be selected depending at least upon the determined resorption rate. Also, a second material can be selected depending upon at least one of the determined bone regrowth rate, the determined force in the region of the anatomy, the determined length of time that the implant should retain a selected strength, or combinations thereof. An implant can be formed of the first material and the second material.

The composite implant materials provide the ability to allow tissue ingrowth into the implant, improved degradation profiles, improved strength retention, elimination of long term degradation complications, and improved biocompatibility with surrounding tissues. Further advantages and areas of applicability of the present teachings will become apparent from the detailed description provided hereinafter. It should be understood that the detailed description and various described embodiments are intended for purposes of illustration only and are not intended to limit the scope of the teachings.

BRIEF DESCRIPTION OF THE DRAWINGS

The present teachings will become more fully understood from the detailed description and the accompanying drawings, wherein.

DESCRIPTION OF THE VARIOUS EMBODIMENTS

The following description of various embodiments is merely exemplary in nature and is in no way intended to limit the teachings, its application, or uses. Although the following various examples may relate to spinal implants, fracture plates, anchors, screws, or the like, other appropriate implants may be formed. Also, although various materials are disclosed for use in various applications, it will be understood that other appropriate materials may also be provided.

Figure 1:
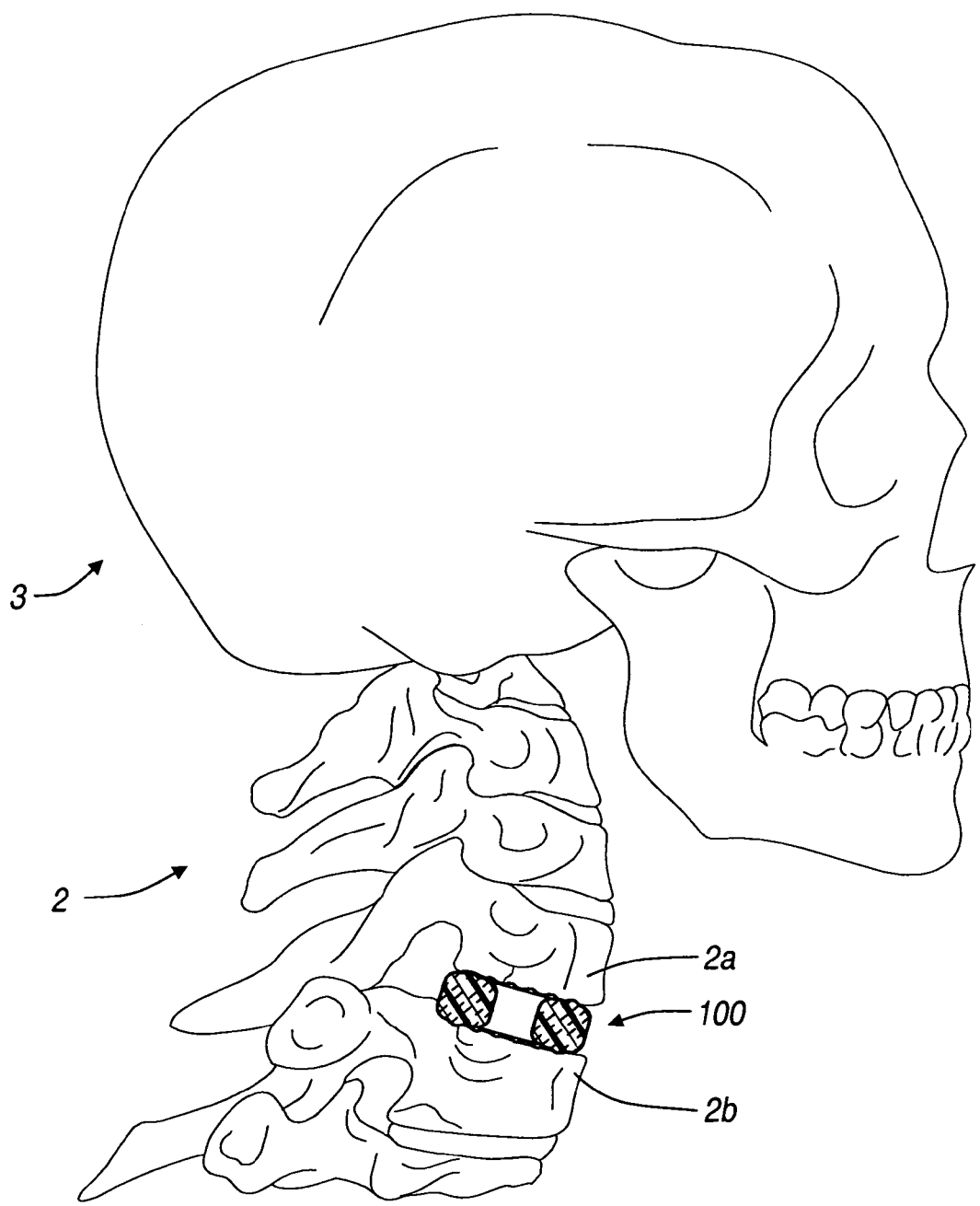
FIG. 1 is a perspective view of an environmental view of an implant according to various embodiments.

An implant 100 (FIG. 9), as illustrated in FIG. 1, may be positioned relative to a selected portion of an anatomy. Various appropriate anatomies include those of a human and may include the cervical spine 2 and a skull 3 of a human. The implant 100 may be a spacer for use in a spinal fusion procedure, as discussed herein. Thus the implant 100 may be positioned between a first vertebrae 2a and a second vertebrae 2b. Although the implant 100 may be used in a spinal procedure, it will be understood that implants according to various embodiments may be formed and used in selected procedures.

Figure 2:
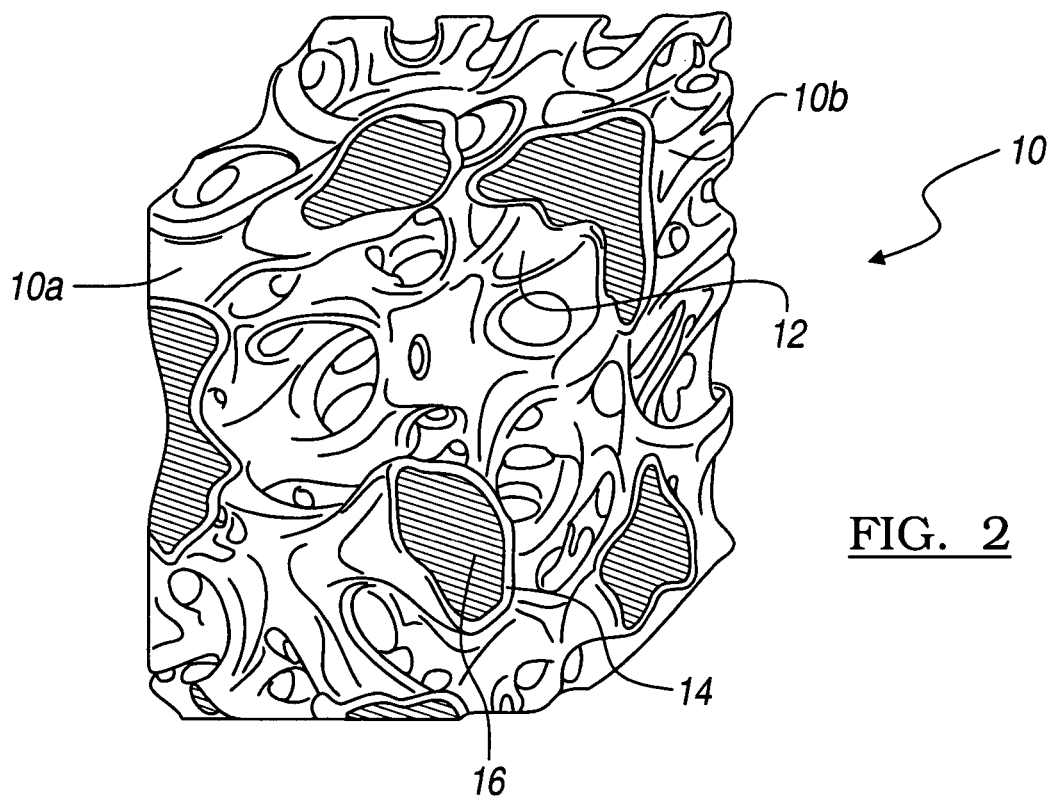
FIG. 2 is a perspective detailed view of a scaffold according to various embodiments.

With reference to FIG. 2, a structure 10 is illustrated. Although the structure 10 may be any appropriate material, it is exemplary a ceramic material such as Pro Osteon 500R. The structure 10 can also be referred to as a scaffold. The scaffold may be used for various purposes, such as supporting or encouraging bone ingrowth when used in an implant. The structure 10 can also be a polymer matrix, or any other appropriate material. The structure 10 can include any appropriate materials, such as biocompatible, bioabsorbable, or any appropriate material. For example, the structure 10 can be formed of a ceramic and generally include a substrate comprising calcium carbonate 12 that is coated with a thin layer of hydroxyapatite 14.

The structure 10 may be formed of natural sources of biocompatible, bioresorbable materials, such as coral. Alternatively, or in addition thereto, various synthetic materials may be used to form the structure 10. These materials may include absorbable ceramics, absorbable polymers, or any other absorbable porous matrix. In various embodiments, the porous material may include the resorbable ceramic sold under the trade name Pro Osteon 500R by Interpore Spine Ltd. (Irvine, Calif., U.S.A.), Calcigen PSI by Biomet (Warsaw, Ind., USA), or OsteoStim by EBI (Parsippanny, N.J., USA). Porous materials useful herein include those disclosed in U.S. Pat. No. 4,976,736, White et al., issued Dec. 11, 1990; and U.S. Pat. No. 6,376,573 White et al, issued Apr. 23, 2002, which are hereby incorporated by reference.

The Pro Osteon 500R material consists of an interconnected or continuous porous calcium carbonate substrate with a thin surface layer of hydroxyapatite. Various other exemplary porous materials may include calcium carbonate, tricalcium phosphate, biphasic calcium phosphate, or any appropriate calcium based ceramic. It will also be understood that the structure 10 may be any appropriate combination and may be formed in any appropriate combination, such as including one material as a coating on another.

Also the structure 10 may be formed from a polymer. A polymer matrix may define a porous structure similar to the structure 10. The material of the polymer matrix may be any appropriate polymer such as a biocompatible, resorbable polymer including those discussed herein. Thus, it will be understood, that the structure 10 may be formed of any appropriate material, including a biocompatible, resorbable ceramic, polymer, composite, etc.

The structure 10 itself may be used for various purposes, such as a bone regeneration scaffold or bone graft replacement. Nevertheless, the physical properties of the structure 10 can be augmented for various reasons. For example, the structure 10 alone may not include a selected physical property, such as a selected compressive strength, tensile strength, torsion strength or the like. Thus, the structure 10 may be augmented to improve its properties allowing for greater use as a surgical device, as discussed herein in various embodiments.

To augment the structure 10, a second material may be added thereto, such as during formation of the structure 10 itself or at a later time. For example, a selected material may be injected into or otherwise provided into a pore 16 defined by the structure 10. The structure 10 can include a channel or plurality of pores 16 that may be a substantially continuous or interconnected pores. The pores 16 may define a plurality of sizes of pores or porous structures. For example, the pores may range from about 0.1 nanometers (nm) to about 1 mm.

The pores 16 define a generally interconnected path or connection throughout the structure 10. Paths or channels can interconnected the pores 16. The interconnected nature of the pores 16 may be referred to as a continuous phase throughout the structure 10 as well. The continuous phase may also be understood to be interconnected pores that are defined by a solid portion of the structure 10. Thus, the channels 16 of the structure 10 are defined by the structure 10 and extend throughout the structure 10. Moreover, the channels 16 generally extend through the structure 10 such that a path can be traced from a first side 10a of the structure 10 to a second side 10b of the structure 10 or from an entrance path to an exit path that can enter and exit from any sides or from the same side.

The pores 16 may be connected with other channels 16 to form the interconnected or continuous pores or channels. Also the various channels may interconnected such that more than a single channel or two openings may be interconnected in the structure 10. It will be understood, however, that the pores 16 may be any opening that allows access to the interior of the material 10. For example there may be interstitial spaces defined between the portions that defined the channels interconnecting other pores. These interstice spaces may also be referred to as pores. Therefore, it will be understood that the pores 16 may be any opening that allows access to the interior of the structure 10 and may be filled with a second material, as discussed herein.

The different sized pores or channels may be used with or are specifically applicable to different types of surgical indications. For example, with reference to FIG. 3, the macropores, such as those generally ranging from about 10 um to about 1 mm, may be filled with a selected polymer 21. If desired, the microporosity, generally in the range of about 0.01 μm to about 1 μm, can be left open and substantially free from any material. The polymer 21 may be injection molded in a semi-liquid, molten form to fill the macroporosity defined by the structure 10, such as the pore sizes that are operable or easily filled with the polymer in a flowable state. Various polymers may be used to fill a selected porosity of the structure 10. For example, bioabsorbable, biocompatible, or any appropriate combination of materials may be used.

It will also be understood that any appropriate number of materials may be provided. Therefore, no only the structure 10 and a polymer 21 may be used. For example, various materials also include those that include therapeutic aspects, such as antimicrobial agents that can be released. Nevertheless, the structure 10 may be filled to any appropriate degree with more than one material.

In addition, the selected polymer 21 may include polylactic acid. For example, a polylactic acid may be provided that includes compositional ratio of about 70:30 poly(L/D,L lactic acid). The specific ratio of various chiral monomers in the polymer is merely exemplary and any appropriate ratio may be used. Nevertheless, herein the 70:30 (L/D,L lactic acid) may be referred to as PLDLLA. Other polymers may include a copolymer of lactic acid and glycolic acid. It will be understood, however, that any appropriate polymer material may be used to form the composite 20. Other bioresorbable, biocompatible polymers include poly(glycolic acid), poly(carbonate), poly(urethane), poly(amino acids), poly(phosphazenes), poly(hydoxyacids), poly(anhydrides), poly(dioxanone), poly(hydroxybutyrate), poly(caprolactone). Also copolymers of these or other appropriate monomers may be used. Further, as discussed above, the structure 10 may be formed of a matrix including these polymers or copolymers.

The selected polymer that may be used with the structure 10, however, may be injection molded or otherwise fill the pores defined by the structure 10. The polymer 21 may fill the pores of the structure 10 to form a substantially solid structure. Nevertheless, the composite 20 may still include a selected porosity or open channels even when filled with the polymer 21. Also, it may be selected to fill the pores 16 less than completely, therefore leaving an open space in at least a portion of the pores even if they may include some of the fill material. For example, pores having a size of about 0.01 μm to about 10 μm may still remain in the composite 20 after the polymer is injected or fills the larger pores or macro pores of the structure 10. The pores that are generally less than about 10 μm, may be herein referred to as micropores or microporosity. The microporosity, however, is not necessary and may not always be present. For example, with various polymer filling techniques, such as polymerization of a positioned monomer, discussed herein, the microporosity may be substantially less or non-existent in the composite material 20. As is generally understood a polymer is generally formed of a single monomer while a copolymer generally includes at least two types of monomers.

The composite material 20 may also be formed with any other appropriate method. Generally the polymer used to fill the selected porosity is added to the structure 10 or otherwise used to fill the porosity of the structure 10. In one embodiment, injection molding is used to force molten polymer into the macroporosity of a porous ceramic structure 10. This can result in the composite material 20 including approximately 5-10% open microporosity. In addition, vacuum impregnation techniques may be used. In this instance rather than producing a positive pressure on the melted polymer, a relatively low pressure is formed in the structure 10 to pull the polymer 21 into the porosity. Further techniques, include solution embedding where the polymer 21 is dissolved and then cast into the porosity.

Also, in situ polymerization techniques where the polymer may be polymerized within the porosity of the structure 10 can be used to form the composite 20. In this embodiment, the structure 10 is submerged in a reaction mixture of a monomer or plurality of monomers, an initiator, and/or a catalyst and then heated to the reaction temperature. The polymer is then formed in situ within the porosity of the structure 10.

According to various embodiments, the composite 20 can include a duel ceramic. The structure 10 can be formed of a first ceramic including a first property and the channels or pores may be filled with a second ceramic, rather than the polymer 21, including a second property. The different properties can include resorption rates, compressive strengths, torsion strengths, or the like. This can be achieved by casting a ceramic slurry into the porosity of the structure 10. The slurry can undergo a chemical reaction to set into a hardened form or it can be sintered to form a rigid ceramic phase.

Other methods of forming the composite material 20 are related to the use of porous polymer matrices as the structure 10. The ceramic material is cast within a porous, polymer matrix structure that forms the structure 10. A polymer matrix may be formed to include a selected porosity and a ceramic slurry may be positioned in the pores of the matrix. The slurry may then be forced to harden to form a solid or porous ceramic phase within the porosity of the polymer structure 10. Thus, the composite 20 may be formed by positioning the polymer in the structure 10 formed of a porous ceramic or by positioning a ceramic in the structure 10 formed of a porous polymer.

Also, two polymers including different properties can be used to form the composite 20. A first polymer including a first property may be used to form the structure 10 that includes a selected porosity and/or channels. The porosity of the structure 10 can be filled with another polymer with a different property. Again, the properties of the two polymers may include a compressive strength, a resorption rate, a tensile strength, or the like. This can be achieved through injection molding, in situ polymerization, and solution casting techniques.

It will be understood that the structure 20 may be a substantially dual phase or greater composite so that it will react in substantially uniform manner when implanted in the body. The phases can refer to the phase of the structure 10 and the phase of the material positioned in the channels 16 of the structure 10, such as the polymer 21. According to various embodiments, the composite 20 may be about 30 weight percent (wt %) to about 70 wt % polymer fill 21 and about 30 wt % to about 70 wt % structure 10. For example, the composite material 20 may be about 55 wt % to about 65 wt % polymer fill 21 and about 45 wt % to about 55 wt % ceramic structure 10. Nevertheless, the composite 20 may be substantially 100 wt % polymer if the structure 10 is formed from a porous polymer matrix. In this case the composite 20 may be about 30 weight percent (wt %) to about 70 wt % polymer fill and about 30 wt % to about 70 wt % porous polymer matrix. The same applies to a substantially 100% ceramic composite composed of a slow and fast resorbing ceramic.

Both phases, that being the structure phase 10 and the fill phase 21 may be substantially continuous. This means, according to various embodiments, that the fill portion 21 is substantially interconnected throughout the composite 20 and that structure phase 10 is also substantially interconnected. This is can be a result of using an intact structure phase 10 rather than a particle. Though, it will be understood, that an appropriate structure phase 10 may be formed from particles. By filling the porosity of the structure phase 10 with a second material 21, the resulting composite 20 is effectively composed of two or more distinct, intact, and continuous phases. As discussed herein, the different resorption rates of the continuous phases 10, 21 within the composite 20 results in a resorption profile that can include a slowly degrading phase and a quickly degrading phase. The quickly degrading phase can allow for tissue ingrowth as the phase is resorbed whereas the slowly degrading phase provides the implant site with mechanical support. It will be understood that either the structure 10 or the fill 21 may be formed to be the quicker resorbing phase.

The composite 20 is the result of filling the macroporosity of structure 10. However, the microporosity of the structure 10 can be left open. This microporosity found in the ceramic phase of composite 20 may, without being bound by the theory, function in that it allows for the absorption of fluid throughout the composite 20 and the diffusion of degradation products out of the composite. This allows the composite 20 to degrade in an even manner from the inside out, results in a gradual transition of load to the newly regenerating tissue. In instances where acid based polymers such as poly(lactic acid) and poly (glycolic acid) are used as the fill phase within the composite, the microporosity in the ceramic allows the acidic products to leave the implant and be absorbed by the surrounding tissue in a timely manner.

Figure 4:
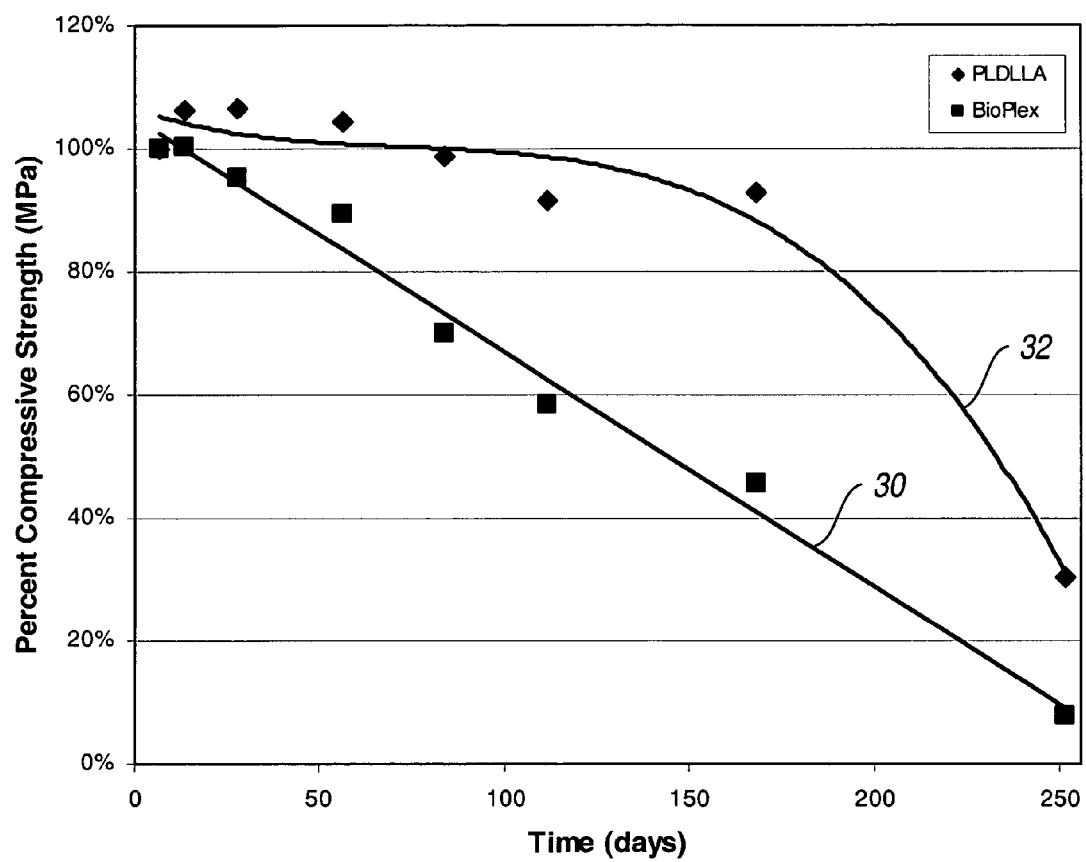
FIG. 4 is a graph showing compressive strength over time of a continuous phase composite and a pure polymer specimen.

As discussed above, the polymer injected into the structure 10 may fill the macroporosity of the matrix 10 but maintain an open microporosity. The effect of this microporosity and/or continuous phase aspects of the composite on the degradation of a continuous phase composite 20 is shown in FIG. 4. The graph in FIG. 4 illustrates the results of an experiment where degradation was conducted in a generally known phosphate buffer solution held at about body temperature (about 37° C.). The degradation profile of a continuous phase composite composed of PLDLLA and Pro Osteon 500R was compared to a pure polymer sample composed of only PLDLLA. In FIG. 4, the graph of compressive strength over time shows a generally even and linear degradation profile of the composite (line 30) when compared to faster drop in strength seen with the pure polymer device (line 32). Although the same polymer was used in both the composite and pure polymer specimens, the graph clearly shows the impact of the composite 20.

As illustrated in FIG. 4, the compressive strength of the pure PLDLLA sample does not change over a significant life span of the implant. Nevertheless, after about 150 days, a drop in compressive strength is illustrated. Therefore, during a majority of the life span of the PLDLLA implant, the compressive strength does not change while near the end of its life span, the compressive strength may degrade rapidly. The more even and linear drop in strength may be selected for various applications. This may allow for an even and gradual loading of an area of the anatomy near the implant of the composite 20.

Examining the composite degradation profile, as illustrated by line 32, the compressive strength of the composite material 20 is substantially linear over its lifetime. That is, that the degradation of the compressive strength of the composite 20 does not include any long periods of maintenance of a single strength, nor a steep drop off at any particular time. A substantially linear decrease in compressive strength over time in the degradative environment, such as an anatomical environment, allows for the gradual loading of healing tissue with additional stresses.

For example, when the implant is used as a bone replacement, it may be desirable to have a substantially continuous increase in stresses relative to the implant. As is known to one skilled in the art, the increase of stresses relative to the bone may increase or enhance bone ingrowth into the area. Particularly, in a resorbable implant, it is desirable to increase or enhance bone ingrowth into the area where the implant has been degraded. As the implant degrades, the stresses are transferred to the surrounding bone, and the new tissue slowly becomes load bearing.

Figure 5A:
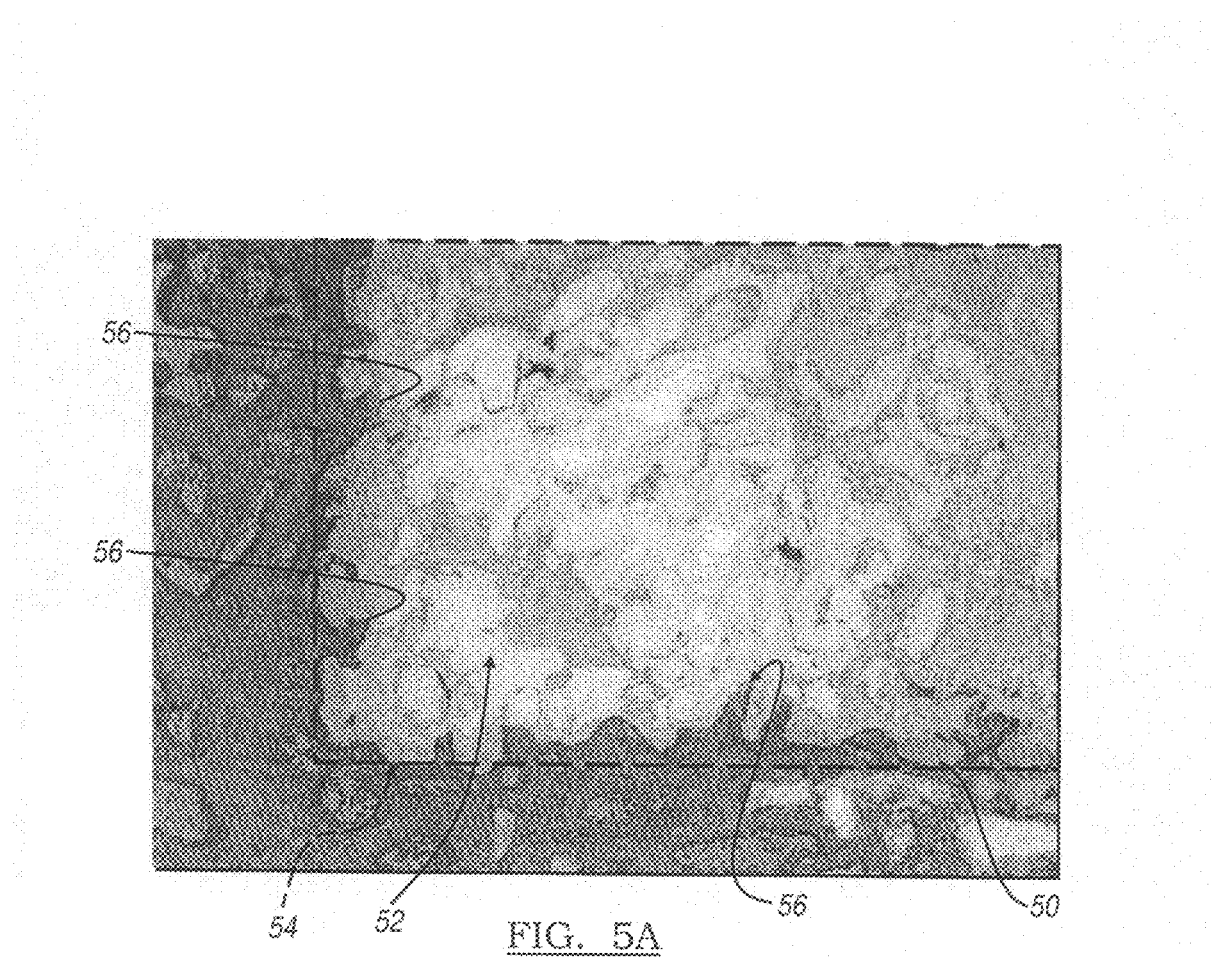
FIG. 5A shows tissue ingrowth into an implant according to various embodiments placed in an in vivo bone defect at 3 months.
Figure 5B:
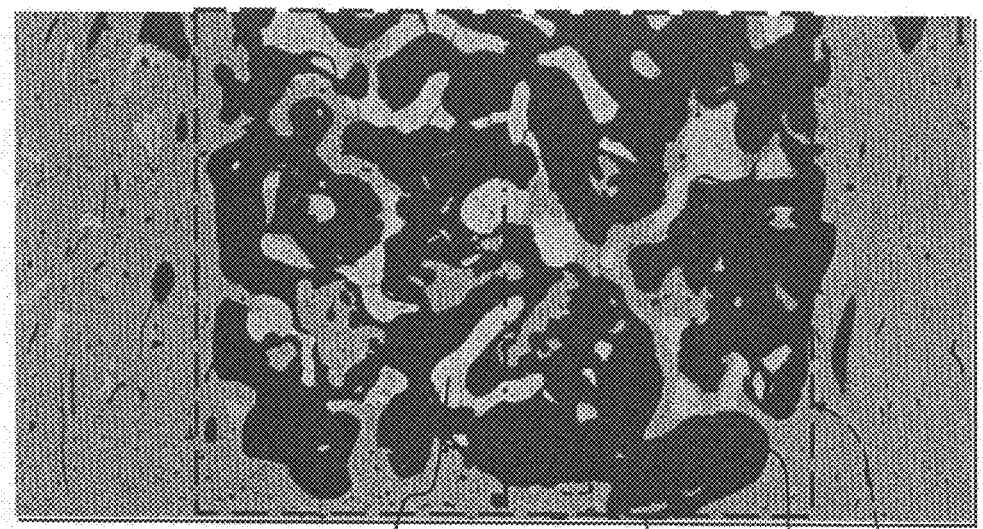
FIG. 5B shows tissue ingrowth into an implant according to various embodiments placed in an in vivo bone defect at 9 months.
Figure 5C:
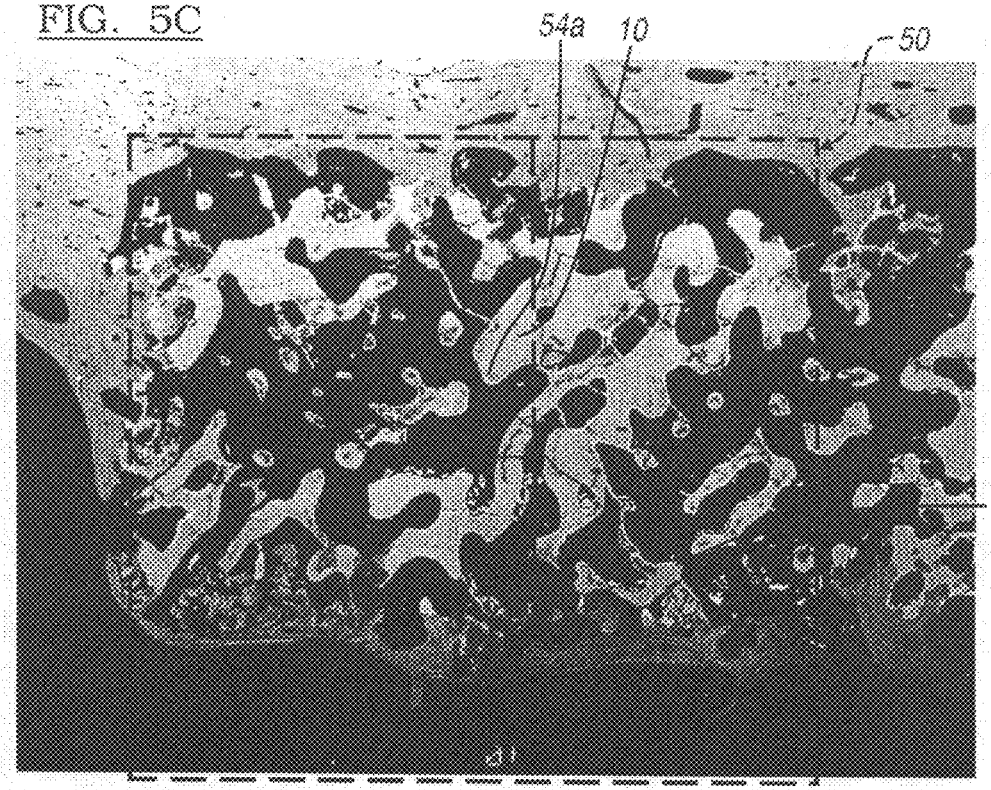
FIG. 5C shows tissue ingrowth into an implant according to various embodiments placed in an in vivo bone defect at 18 months.

In various embodiments, the composite material 20 has exhibited a linear decrease in strength as shown FIG. 4. In addition to the benefits of a gradual transfer of forces to the new tissue, the continuous phase composite also demonstrates superior for tissue ingrowth into the implant. This ability was demonstrated in a load bearing bone defect model in the tibia and femur of sheep. In such a model, typical solid polymer implants may show bone formation in limited amounts on the surface of the material. With the continuous phase composite 20, the resorption of the ceramic phase allowed eventual bone into the center of the implant wall. In this study a generic implant cage was fabricated with a central area designed to hold bone graft materials and was implanted into the tibia and femur of sheep. The implant 52 generally included Pro Osteon 500R formed into a composite with PLDLLA. As seen in FIG. 5A-5C, back scattered electron microscope images demonstrated the gradual penetration of bone into the implant from 3 to 18 months.

With reference to FIG. 5A, the outer edge of the implant 52 is illustrated by phantom line 50. This 3 month image shows a continuous layer of bone 54 covering the entire implant surface and additional bone 56 penetrating approximately 300 um into the implant material 52. The penetration of bone within the device 50 can be the result of resorption of the structure phase 10 of material 52, which allowed bone ingrowth into various spots shown in 56.

As illustrated in FIG. 5B, at about 9 months, the implant material is substantially more degraded and large amounts of bone ingrowth are seen. As illustrated in FIG. 5B, bone, particularly new bone 54A, has grown deep into the implant area 50. The new bone growth 54A is substantially next to and intermixed with the ceramic structure 10 of the composite material. Further, portions of the polymer material 58 are being degraded as well.

With reference to FIG. 5C, the implant 50 is quite degraded in vivo after about 18 months. Again, the new growth bone material 54A is growing deep into the implant area. Even further, it is growing substantially next to or adjacent various portions of the construct material 10, while the polymer material 58 is also being actively degraded.

Figure 6:
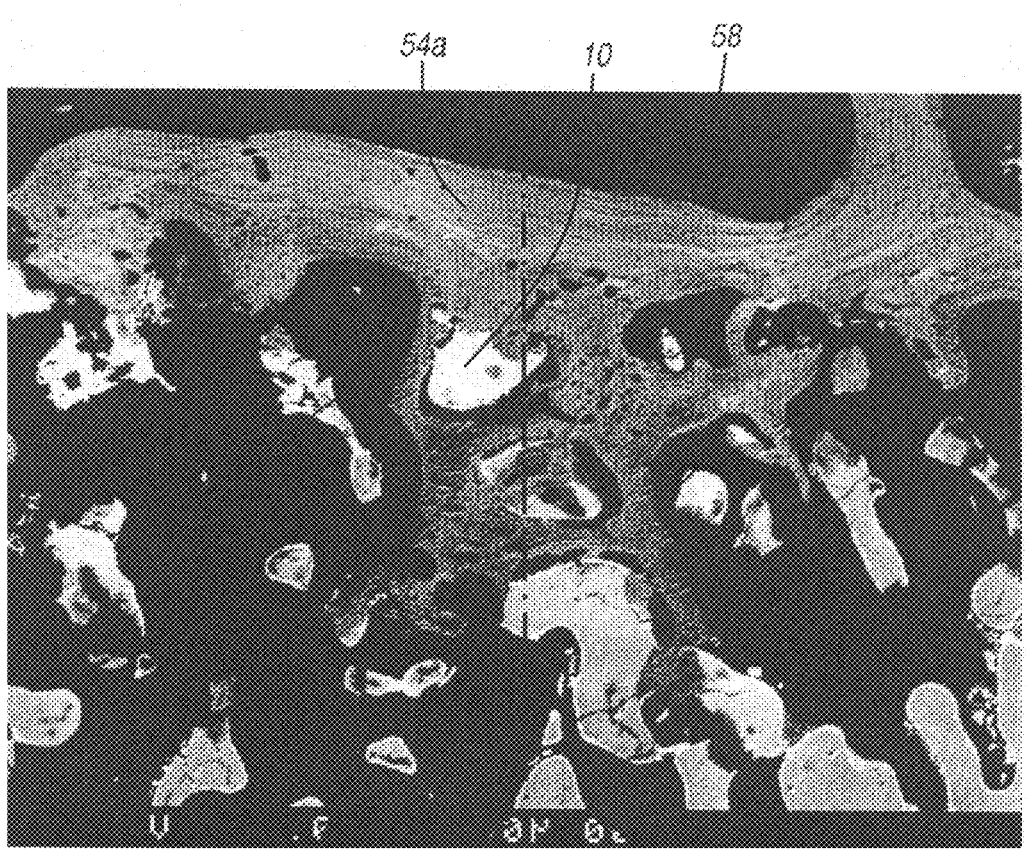
FIG. 6 is a detailed view of the replacement of a large portion of the continuous phase composite with normal bone at 18 months.

FIG. 6 shows a further example of the 18 month degradation response. This image shows new bone growth 54A occurring substantially adjacent to the original implant material, including the structure 10. This indicates that significant portions of the polymer 58 have been replaced by bone. The image clearly shows new bone growth 54A in areas once filled with polymer indicating the lack of any implant complications.

Further, the image in FIG. 6 shows portions of bone 54A intermixed with areas of residual ceramic matrix 10. In this exemplary embodiment including Pro Osteon 500R as the structure 10, the residual portions of ceramic structure 10 are substantially composed of calcium carbonate. The interaction of calcium carbonate and lactic acid from the polymer phase 58 results in a self-neutralizing reaction that eliminates some of the acid released from the degrading implant. This phenomenon further improves the long term biocompatibility of the device as seen by bone formation in areas of active lactic acid degradation.

In addition to the self-neutralizing ability of the composite, the presence of vascularized bone and residual microporosity also add to the overall biocompatibility of the degrading composite. This tissue and pore system serves as a means to transport degradation products from the site to the bloodstream. The blood vessels within the implant and the microporosity system allow degradation by-products to be cleared from the implant area in a timely manner.

Figure 7:
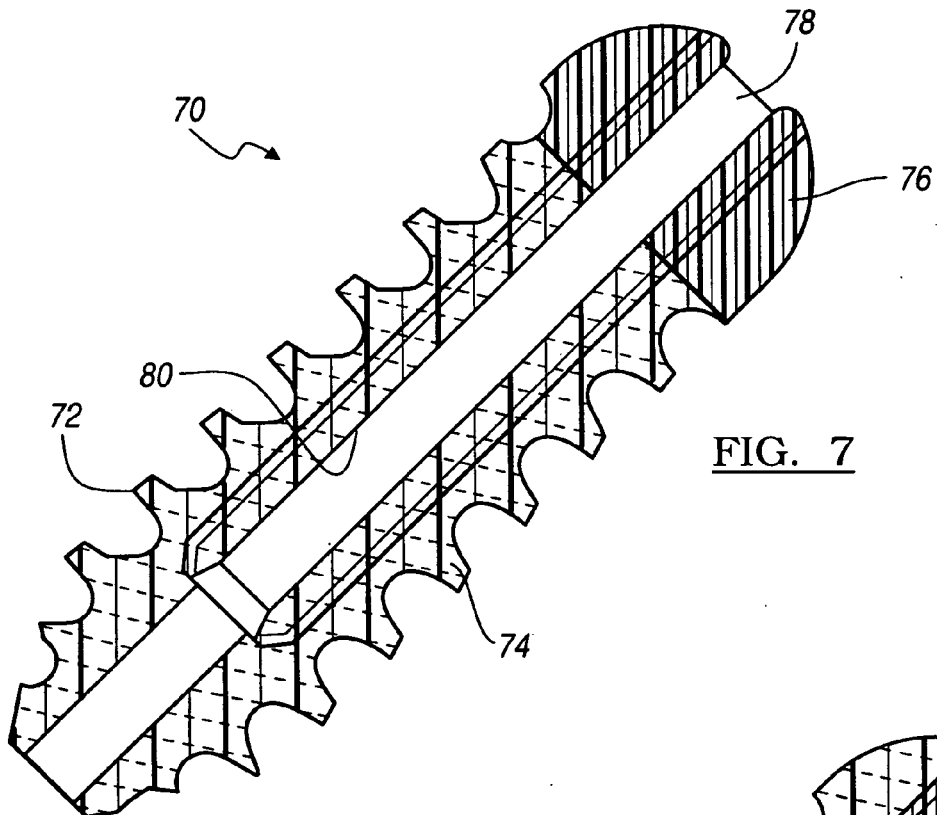
FIG. 7 is an implant according to various embodiments.

With reference to FIG. 7, an implant 70 is illustrated. The implant 70 demonstrates the versatility of the fabrication process by machining devices with both a composite region 74 and a polymer region 76. For example, the implant 70 may include an external thread or engagement portion 72 composed of the continuous phase composite 74 similar to the composite 20. However, implant 70, can be machined from a composite block with an excess polymer region. This results in a dual region implant with a polymer head 76 and a composite base 74. Therefore, the composite portion 74 may be formed from a ceramic material, such as the Pro Osteon 500R, that has been reinforced or injected with a polymer, such as the PLDLLA. Also, the polymer portion 76 may be molded to the composite portion 74 according to various embodiments.

In addition, the polymer portion 76 may be composed of 100% PLDLLA. Such an implant can improve the mechanical properties of the device for various applications. For example, the second portion 76 including only the polymer region, may provide a torsional strength that is greater than the torsional strength of the composite portion 74. Therefore, a tool engaging portion or area 78 may be formed in the polymer portion 76 to allow for a greater torsional force to be applied to the implant 70 that may not be satisfied by the composite portion 74.

Figure 8:
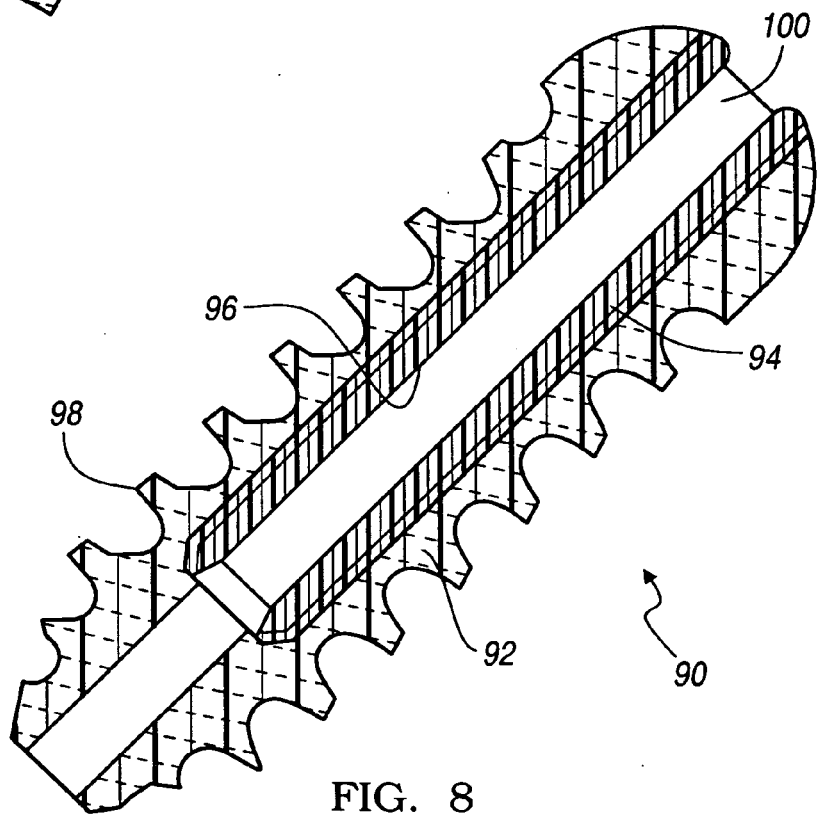
FIG. 8 is an implant according to various embodiments.

With reference to FIG. 8, an implant 90 may be provided for similar purposes. The implant 90 can also include two portions, such as a composite portion 92 and a polymer portion 94. The composite portion 92 may be substantially similar to the composite material 20 illustrated in FIG. 3. The addition of the polymer portion 94 to the central area of the composite portion 92, however, can be used to achieve selected properties of the implant 90.

With regard to the fabrication of implant 90, this orientation of polymer 94 and composite 92 can be fabricated by drilling holes within the porous structure 10 and then subjecting the structure 10 to one of the composite fabrication techniques. The addition of the polymer phase 21 to the structure 10 with holes, such as through injection molding, results in filling of the holes in addition to creating the composite. During the machining of the implant, the device 90 can be centered around the central polymer region 94 to define a bore 96 through the implant 70. The resulting implant will have a central polymer bore 94 surrounded by a composite region 92.

The implant 90 may be used for any appropriate purpose, and an engagement portion 98 may be formed on an exterior thereof. The engagement portion 98 may be used to engage various structures, such as bony portions, such that the implant 90 may be an anchor or may define a screw. Further, a tool engaging structure 100 may be defined in the polymer portion 94 for allowing engagement of a tool with the implant 90 for positioning the implant 90 in various anatomical locations. As discussed above, the implant 90 may be used for various purposes, similar to the purposes for the implant 70. Therefore, the implant 90 may be used as a bone anchor, a suture anchor, a soft tissue anchor, fracture screw, or any appropriate portion. Further, the implant 90 may be used for any other appropriate procedure or implant.

Implants, such as the implants 70, 90 according to various embodiments may be formed in many different ways and include different structures. Those described above are merely exemplary in nature and not intended to limit the teachings herein. For example, an implant 70,90 may include an exterior "thin" coat formed around a polymer interior, or vice versa. The thin coat may include a thickness that is substantially less than that of the interior portion, but provide selected properties to the implant. That is, the implant may be formed in any appropriate manner and for various purposes. Also a portion of the polymer may be placed as a seam or flex point in an implant with the composite or other material surrounding it.

Various other types of implants include sheets formed of the composite 20, for example implants that include a surface area greater than a thickness. Additionally, reinforcing ribs or struts composed of polymer can be added to the composite device in order to provide an improvement to the required mechanical properties. Also, tacks, bone fusion devices, bone graft devices, cement restrictors, intramedullary pins, and other implants may be formed from combinations of the composite 20 and polymer regions. Thus, one will understand that the implants described herein are merely exemplary.

Figure 9:
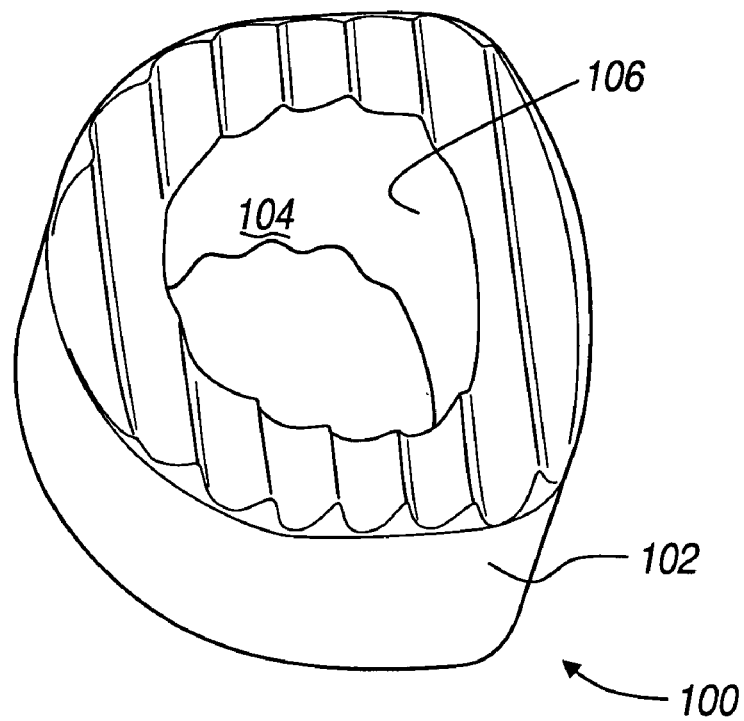
FIG. 9 is a perspective view of an implant according to various embodiments.

With reference to FIG. 9, a spinal implant 100 is illustrated. It will be understood that the implants, according to various embodiments, may be positioned between any appropriate vertebrae. Therefore, discussion of a first vertebrae and a second vertebrae is not necessarily C1 and C2 or any other specific set of vertebrae, unless do discussed. The spinal implant 100 may be for any appropriate spinal application, such as an intervertebral spacer for cervical fusion. The cervical spine implant 100 may include a ring or open structure including an exterior wall 102 and an interior void 104. The interior 104 may be defined by an interior wall 106. The purpose of the interior void can be to contain bone graft materials such as autograft, or allograft.

Additionally, the structure 10 can act as a bone growth scaffold it can also be added to the void 104. This would result in an implant including a central portion of the structure 10 and the composite 20 surrounding it. This would allow the composite 20 to support the surgical site while the graft or structure material 10 can allow for immediate ingrowth.

The cervical spine implant 100 may be formed in any appropriate manner. For example, a block of material formed of the composite 20 may be machined into a shape of the implant 100. Alternatively, the material forming the structure 10 can be machined into the cervical spine implant 100 shape and then filled with the polymer material to create the composite 20. Additionally, the implant 100 may include any appropriate dimensions, such as a selected length, width, height and depth. Further, the implant 100 may be formed to include an angle, such that a first side of the implant 100 may be taller than a second side of the implant 100. Regardless, the spinal implant 100 may be implanted into a the cervical spine, such as to assist in fusing one or more cervical vertebrae.

Figure 10A:
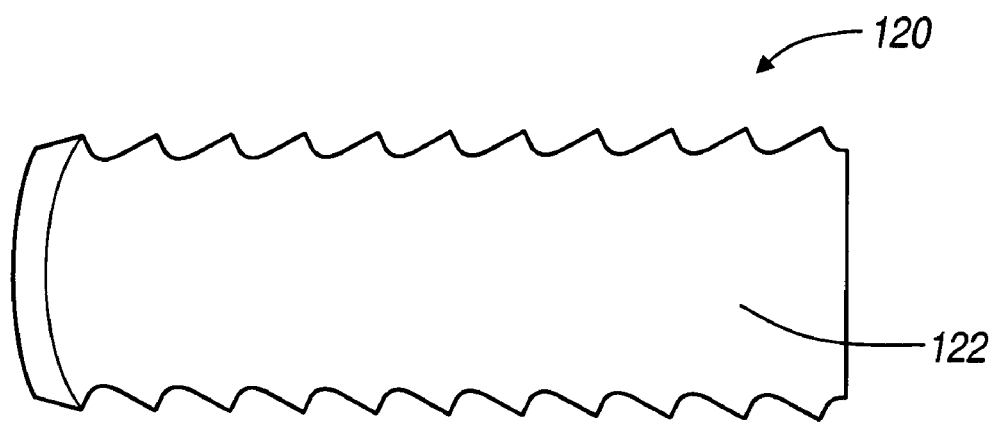
FIG. 10A is a plan view of an implant according to various embodiments.
Figure 10B:
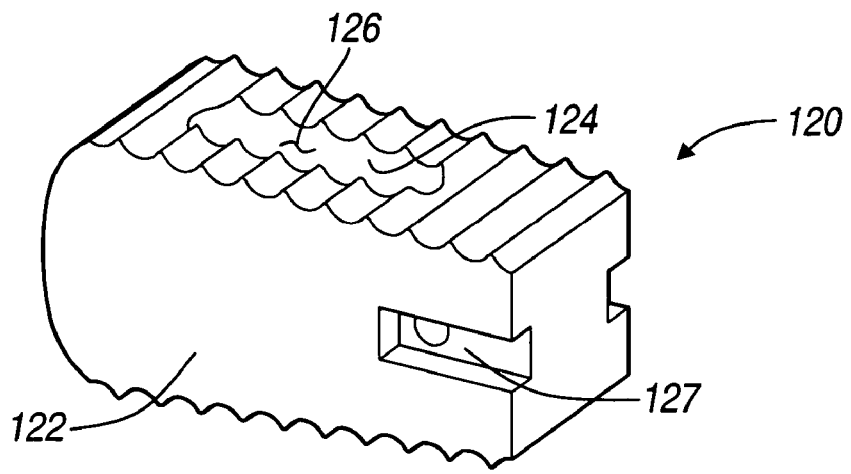
FIG. 10B is a perspective view of an implant according to various embodiments illustrated in FIG. 1A.

With reference to FIG. 10A and FIG. 10B, a lumbar spinal implant 120 for posterior lumbar interbody fusion (PLIF) is illustrated. The PLIF implant 120 may be formed according to any appropriate dimensions. For example, the PLIF implant 120 may include a selected length, height, depth, or other appropriate dimensions. Further, as discussed above, the spinal implant 120 may be formed of the composite 20 or may be formed of the structure 10, and then filled with the selected polymer. Regardless, the PLIF implant 120 may be formed according to various specifications for a selected procedure.

Further, the PLIF implant 120 may include an exterior wall 122 that may define a structure including an interior wall 124 that defines an opening 126 that can be used to contain graft materials. The PLIF implant 120 may therefore be formed to fit or be implanted into a selected portion of the anatomy, such as a spinal fusion procedure. The PLIF implant 120 may be positioned in a selected portion of the spine, such as the thoracic portion, a lumbar portion, or a sacral portion, such as to assist in fusing one or more lumbar vertebrae. The PLIF implant 120 may also include a grasping region 127. The grasping region 127 may be defined as a groove or detent in the implant 120. The grasping region 127 may be grasped with an appropriate instrument, such as a forked instrument, for positioning and holding the implant 120 during implantation or other procedures.

Figure 11:
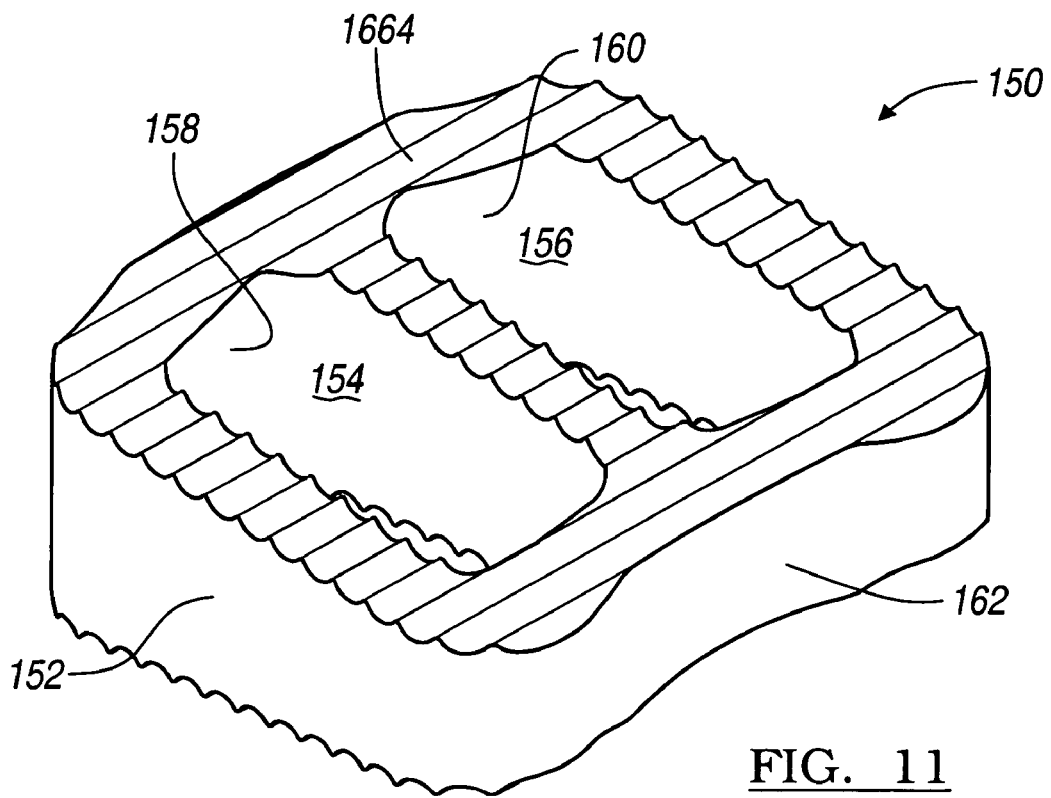
FIG. 11 is a perspective view of an implant according to various embodiments.

With reference to FIG. 11, a spinal implant 150 for anterior lumbar interbody fusion (ALIF) is illustrated. The ALIF implant 150 may include an exterior wall 152 and two interior portions 154 and 156. The first interior portion 154 may be defined by an interior wall 158. Similarly, the second interior area 156 may be defined by a second wall 160. Therefore, the ALIF implant 150 may include two interior voids or openings 154, 156 for containing bone graft materials. Further, the ALIF implant 150 may include a first side 162 that includes a height that is less than a second side 164. The height difference may provide the ALIF implant 150 to be formed at a selected angle for various purposes. For example, the ALIF implant 150 may be positioned through an anterior lumbar approach to assist in fusing one or more lumbar vertebrae.

Spinal implants, such as the implants 100, 120, and 150, or any appropriate spinal implant may include selected materials to form the implants. As discussed herein the materials may be selected for a selected strength or strength degradation. Also the materials for the implant may be selected for a selected bone ingrowth.

Figure 12:
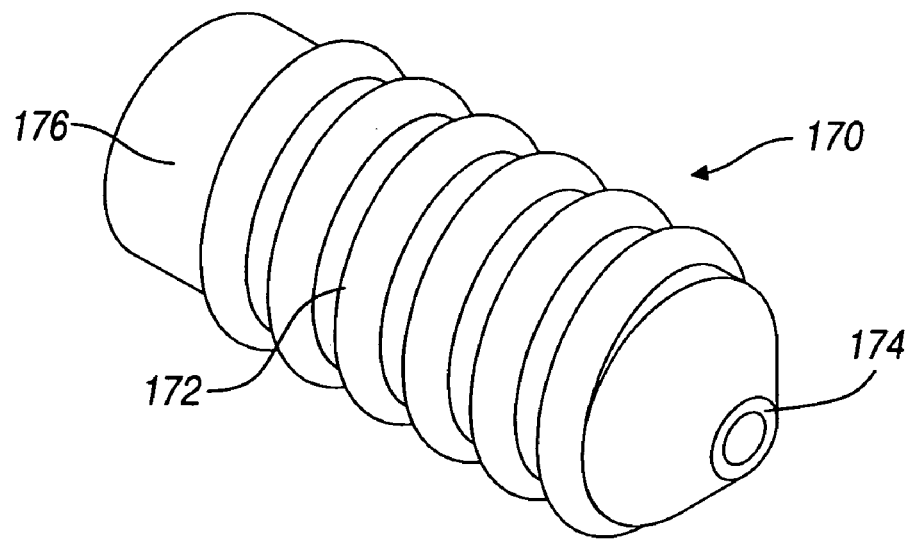
FIG. 12 is a perspective view of an implant according to various embodiments.

With reference to FIG. 12, an implant 170 is illustrated. The implant 170 may define a screw or anchor portion that may be positioned relative to a selected portion of the anatomy. The implant 170 may define a thread 172 that extends along a length of the implant 170 from a first or insertion end 174 to a second or driving end 176. The thread 172 may or may not extend the entire length of the implant 170.

Regardless, the implant 170 may define the thread 172 and the driving portion 176 such that the implant 170 may be inserted into a selected portion of the anatomy. Similar to the implants 70, 90 illustrated in FIGS. 7 and 8 above, the implant 170 may be used to fix a selected soft tissue therein, fix a suture thereto, or other appropriate procedures. For example, in a generally known anterior cruciate ligament replacement, the implant 170 may define an interference screw to assist in holding the graft in a selected position.

The implant 170 may be formed substantially completely of the composite material 20. It will be understood that the implant 170 or the implants described above according to various embodiments, may be provided for various procedures or purposes. As is generally understood in the art, a graft may be positioned or provided of soft tissue to interconnect a femur and a tibia. The implant 170 may be used to substantially hold the soft tissue portion relative to a selected portion of the anatomy. As discussed above, the composite material forming the implant 170 may be absorbed into the anatomy at a selected rate to allow for bone ingrowth and fixation, such as a generally anatomical fixation, of the soft tissue may be provided.

Figure 13:
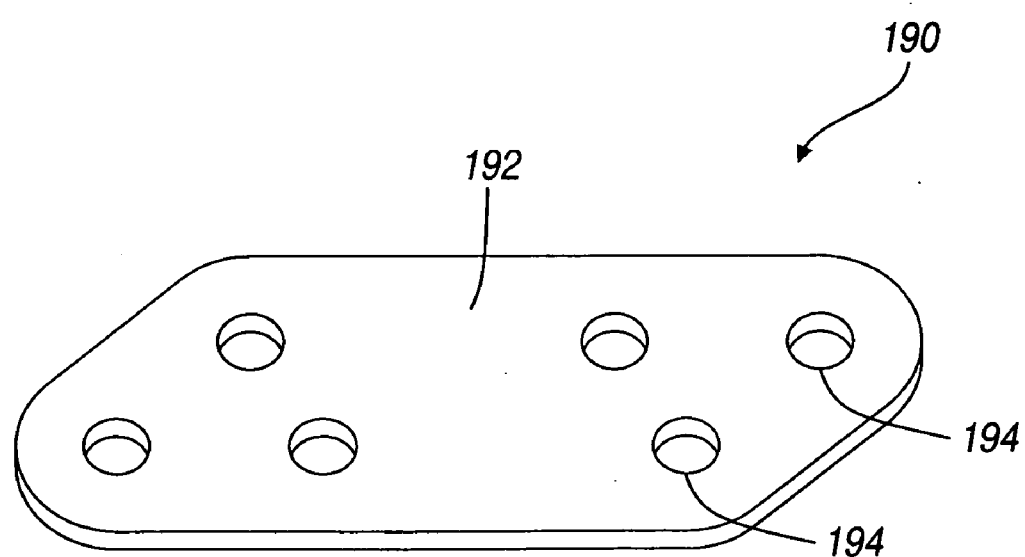
FIG. 13 is a perspective view of an implant according to various embodiments.

With reference to FIG. 13, an implant 190 is illustrated. The implant 190 may generally include or define a structure that is substantially planer and includes a first surface 192 and a second surface opposed therefrom. The implant 190 may include a selected thickness that is substantially less than a surface area of the surface 192. Therefore, the implant 190 may generally be described as a plate or strut. The implant 190 may include any appropriate geometry such as a trapezoid, rectangle, square, or the like. Further, the implant 190 may define bores or holes 194. The bores 194 may be provided for various purposes such as fixation with fixation members, including screws, pins, and the like.

The implant 190 may be used for various purposes, such as fracture fixation, where the implant 190 may be used stabilize bone fragments and to assist in healing of the fracture site. The implant 190 may also be used as a graft retaining plate or structural support during spinal fusion procedures The implant 190 may be formed to include a selected rigidity or strength, as discussed above, for assisting in the bony structure healing. As previously discussed, the implant may or may not contain polymer regions attached to the composite to improve the bending resistance and rigidity of the device or to impart a polymer seam that would provide flexibility. For example, a support portion of the polymer material 21 may be placed or formed along a length or other dimension of the implant 90 to achieve a selected strength or other property.

Additionally, implant 190 in FIG. 13 may also be used for soft tissue fixation as a buttress plate. In soft tissue fixation procedures, sutures are often used to affix the tissue to bone. The thin cross section of the suture, however, may not provide a selected result after implantation. The implant 190 may be used to assist sutures in achieving a selected result in various applications. The plate may provide a surface to abut the suture and protect other tissues, if appropriate. Therefore, a soft tissue implant may include a structure substantially similar to the implant 190 illustrated in FIG. 13. Therefore, the implant 190, according to various embodiments, may be used to repair a selected portion of soft tissue, such as a rotator cuff. The implant 190, however, may be formed to repair any selected portion of the soft tissue, such as a muscle portion, a tendon, a ligament, a dermal portion, or the like.

Figure 14:
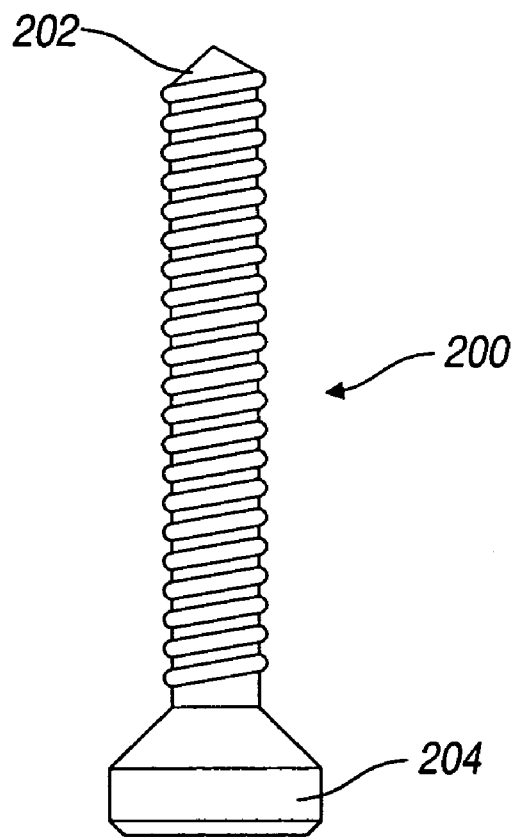
FIG. 14 is a plan view of an implant according to various embodiments.

Similar to the plate 190 in FIG. 13, an implant 200 in FIG. 14 can be used for fracture repair. As discussed above, the implant 190 may be formed to allow for fixation or holding of selected bony portions during a healing process. Other implant portions, such as the implant 200, may also be used to fix or hold selected bony portions at the fracture repair site. The implant 200 may include an extended shaft that defines a thread 202 along all or a portion of the shaft. A driving portion 204 may also be provided to assist in driving the implant 200 into the selected implant site. The thread 202 defined by the implant 200 may be driven into a pre-formed bore, a tapped bore, an untapped bore, or any predefined void. Further, the implant 200 may be formed in appropriate dimensions, such as a length, thickness, thread height, etc., to achieve selected results. The implant 200 may also be cannulated and have a similar composition to the dual region devices 90 of FIG. 8.

Figure 15:
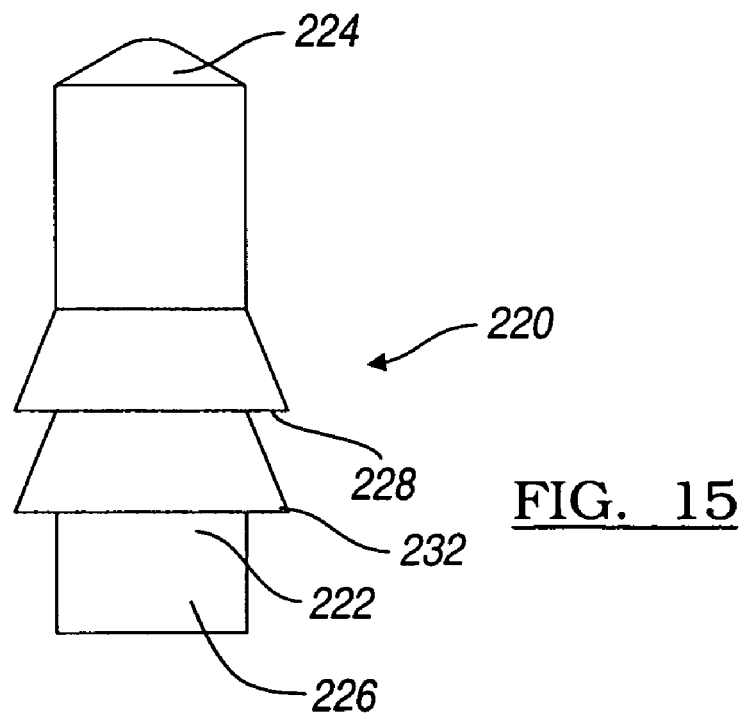
FIG. 15 is a plan view of an implant according to various embodiments.

With reference to FIG. 15, an implant 220 is illustrated. The implant 220 may include a suture anchor or define a suture anchor to assist in holding a selected suture 222 used in soft tissue repair. For example, the suture 222 may be to reattach a soft tissue region to bone or other soft tissue. The implant 220 may define a shaft or body including a first end 224 and a second end 226. The body of the implant 220 may further have a first engaging or interference portion 228 extending therefrom. Further, a second interference portion 230 may also be provided.

The implant 220 may then be driven into the bone of the soft tissue fixation site. The suture 222 is then used to affix the soft tissue to bone. The implant 220 may be generally driven into a bore formed in the portion of the anatomy including a diameter less than a diameter or dimension of the interference members 228, 230. Therefore, the implant 220 may form an interference fit with a selected portion of the anatomy to hold the suture 222 relative to the selected portion of the anatomy.

Figure 16:
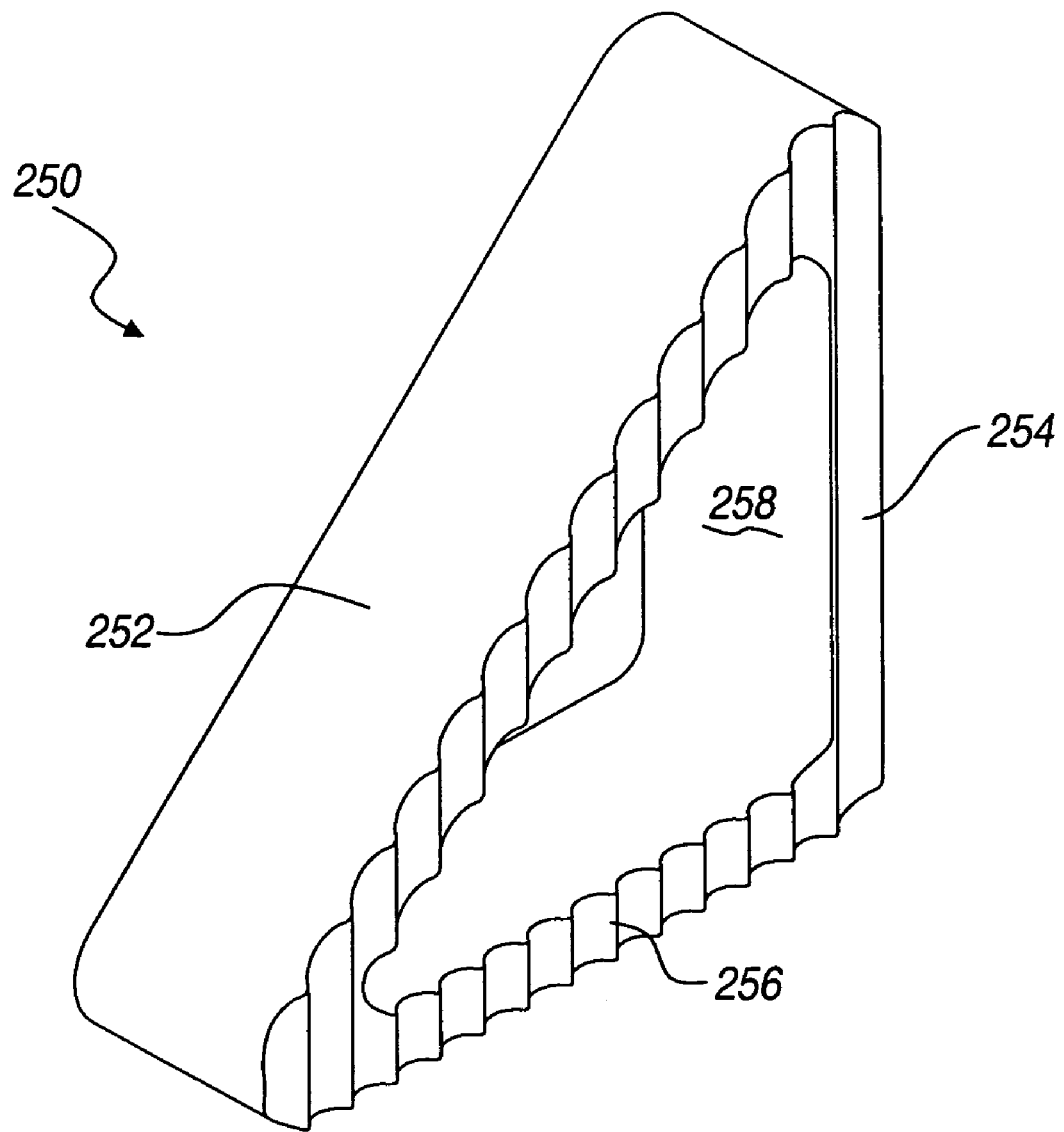
FIG. 16 is a perspective view of an implant according to various embodiments.

With reference to FIG. 16, an implant 250 is illustrated. The implant 250 may include any appropriate configuration, for example, the implant 250 may be formed as a wedge or triangle. Although exemplified as a triangle, the wedge may have any shape. The implant 250 may further define an interior void or open portion 258 for the containment of bone graft materials. For example, as discussed herein, the open portion 258 may be filled with a selected bone graft material, such as an autograft or allograft, or a porous bone growth scaffold for promoting bone healing at the site.

With reference to implant 250, the device may be used in structural grafting applications in areas such as the foot and ankle, tibia, femur, and pelvis where structural support is desired in addition to bone regeneration. The implant 250 may be filled with a selected material 262 that has been positioned in the open portion 258.

As illustrated above, the continuous phase composite material 20 may be formed in the plurality of configurations for various purposes. Further, as also discussed above, the structure 10 may be formed into a selected shape, orientation, geometry, or the like and then filled with a polymer.

Similarly, it will be understood, that the final implant shape may be established inter-operatively to provide a custom fit to the surgical site. For example, the bone graft wedge of implant 250 illustrated in FIG. 16 may need to be augmented due to an anatomy of a patient determined during an operative procedure. Therefore, a user, such as a surgeon, may use powered surgical instruments such as a burrs, drills, osteotomes, grinders, or other tools to substantially customize the implant for the selected patient. Therefore, the implant may be provided either as a blank or in a general shape for eventual customization by the user during a clinical procedure. This may assist in providing a selected result for a patient and decrease healing time, complications, or the like.

Figure 17:
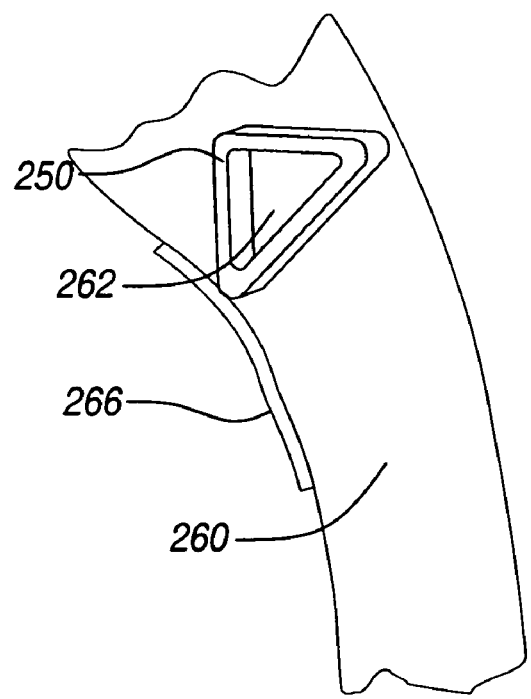
FIG. 17 is a perspective environmental view of the implant in an anatomy.

The implant 250, whether customized or not, may be used in a procedure such as to replace a selected portion of a bone 260. The implant may be filled with the graft material 262 to fill a void that may have formed in the bone 260. A further plate 266 (see FIG. 17) may also be used in the procedure. However, the implant 250 may allow for a selected load bearing for a selected period of time and allow for bone ingrowth into the implant area.

Figure 18:
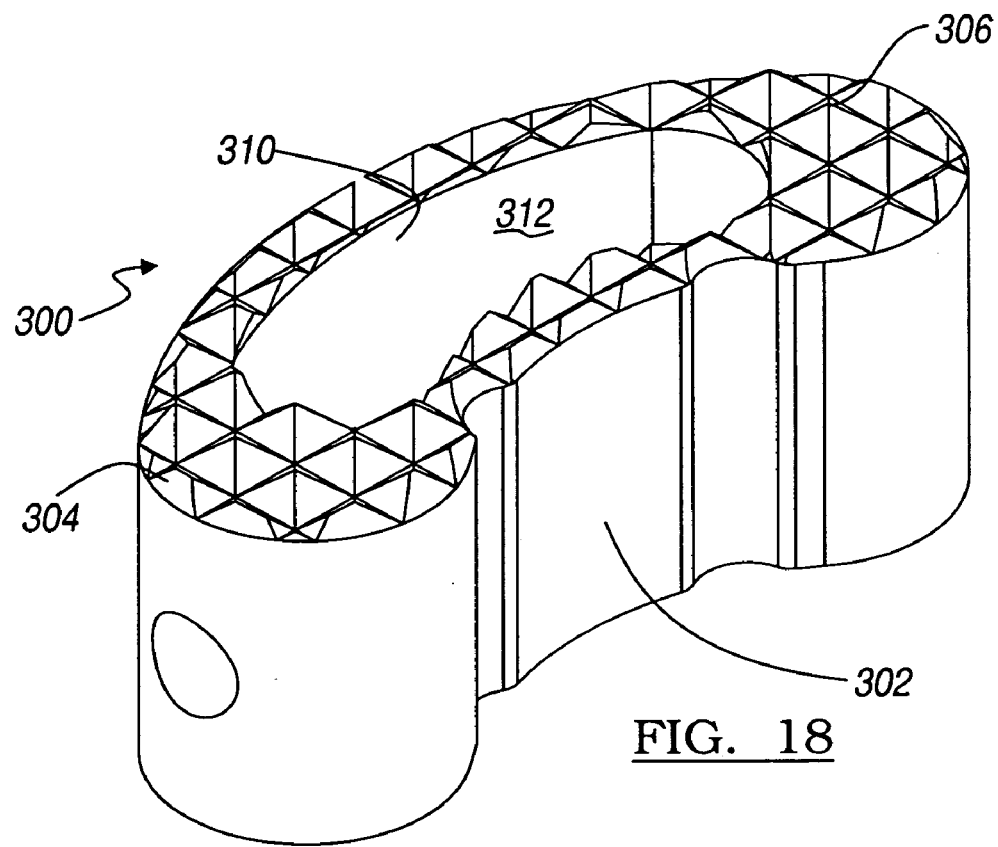
FIG. 18 is a perspective view of an implant according to various embodiments.

With reference to FIG. 18, an implant 300 is illustrated. The implant 300 may be used for a thoracic procedure, or any appropriate procedure. The implant 300 may include an exterior wall 302 and also a top portion 304. The top portion 304 may also define teeth or other fixation portions 306 to assist in maintaining the implant 300 in a selected position. An interior wall 310 can also define an interior void 312. The interior void may allow for positioning of graft material during an implantation. The implant 300, however, may include any appropriate dimensions for a selected procedure. The implant 300 may be used as a disc replacement in a selected procedure, such as in a spinal fusion procedure.

Figure 3:
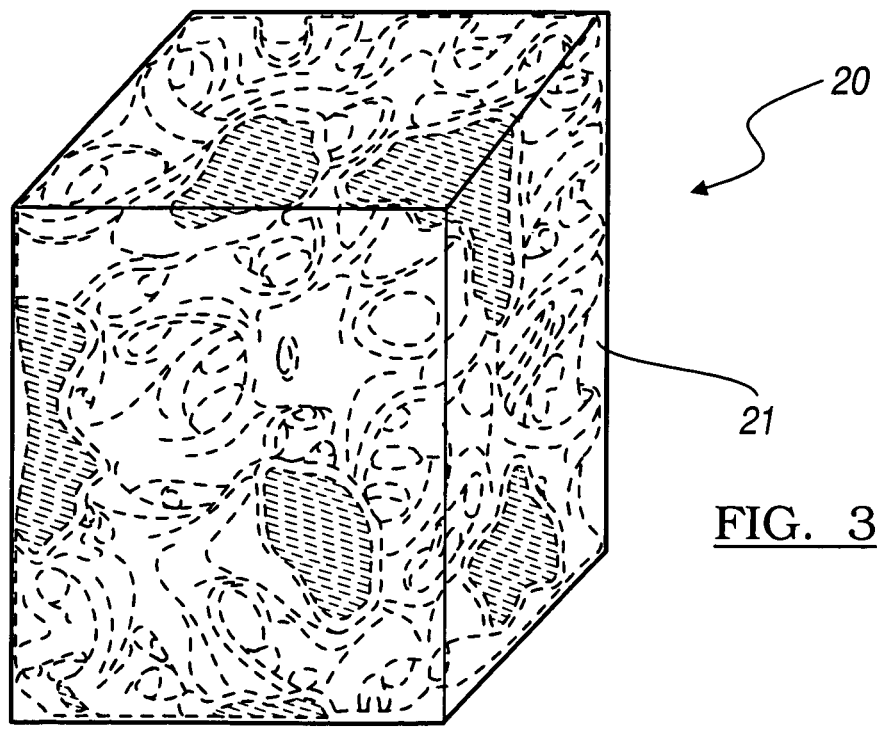
FIG. 3 is a perspective detailed view of a continuous phase composite according to various embodiments of the invention.

Therefore, it will be understood that the composite 20 illustrated in FIG. 3 may be used for any appropriate procedure. The materials chosen to create the composite 20 may be selected from a range of biocompatible and bioresorbable materials to give properties specific to the surgical application. In addition, the fabrication of composite implants with pure polymer or ceramic regions may also provide specific properties based on the application. The composite 20 may be formed into any appropriate implant, such as a structural bone graft, a fixation device, an interbody spinal implant, a prosthesis, or any appropriate implant. Devices for cartilage, tendon, and ligament repair, vascular prostheses, tissue engineering devices, and other medical implants also fall within scope of the continuous phase composite. Therefore, the examples provided above are merely exemplary and not intended to limit the scope of the teachings herein.

Various different material combinations may be used to form the composite 20. The various different combinations of materials may be selected for different purposes and applications, such as where an implant may be positioned in the anatomy. For example, with reference to Table 1, different applications of the implant may include a different selected property. The selected property may be formed or incorporated into the composite material from which an implant may be made depending upon the combination of materials and selected materials used to form the composite 20.

TABLE 1

| Application | Implant Type | Selected Property |
| --- | --- | --- |
| Spinal Fusion | Interbody spacer | Compressive strength, impact resistance |
| Fracture fixation | Fractures screws, pins, rods | Torsion, bending, pull out strength |
| Fracture fixation | Fracture plates | Bending, tension |
| Soft tissue fixation | Interference screws | Torsion, pull out strength |
| Soft tissue fixation | Suture anchors | Torsion, pull out strength |
| Structural bone grafts | Bone graft wedges, bone graft containment devices | Compression, impact resistance |

For example a procedure may be selected to include a selected property, such as a compressive strength after a selected time period after implantation. For example, a spinal fusion implant may be selected to include about 1500 N to about 3000 N of compressive strength at least about six months after implantation. This may be selected for various purposes, such as the amount of time generally necessary for bone ingrowth to form a selected fusion. Therefore, a selected material may be chosen for the polymer 21 of the composite 20. For example, the PLDLLA polymer, discussed above, may form about 60% of the composite 20 with about 40% of the composite 20 being the structure 10 formed of the Pro Osteon 500R. Such a combination can achieve a compressive strength of about 1500 N to about 3000 N at about 6 months after implantation. Although other polymers and other structures 10 may be used to achieve similar results.

In other applications, a fast resorption of the composite 20 may be selected. For example, in a fracture healing or repair may be faster than in a fusion. Therefore, an implant that is substantially resorbed after about 3 to about 6 months may be selected. Such an implant may be formed with a copolymer of lactic acid and glycolic acid. The copolymer can be about 85% lactic acid and about 15% glycolic acid, similar to the material sold as Lacotsorb™ by Biomet, Inc. An implant including such a copolymer as about 60% of the composite while the other about 40% is formed of the Pro Osteon may be used in a fracture situation. For example, the screw 170 may be formed of such a composition for use in an Anterior Cruciate Ligament replacement procedure to provide a selected time when the graft is no longer held with the implant screw 170.

Also the polymer, or slower resorbing material, may be selected based upon inherent properties or ones formed therein. For example, a slower resorbing polymer may generally be one including a higher molecular weight. Thus, the slower the implant should resorb or the longer a selected property, such as compressive strength is needed, the higher the molecular weight may be chosen for the polymer. However, it will also be understood that selected polymers may include properties that may be achieved at lower molecular weights. Also selected strengths of the polymer may be inherent in the polymer itself, rather than a selected molecular weight thereof.

The composite 20 may be formed according a plurality of methods, as discussed above. Although the composite may also be formed to include a selected material contained therein. As discussed above, graft material may be positioned in an implant formed of the composite 20.

Figure 19:
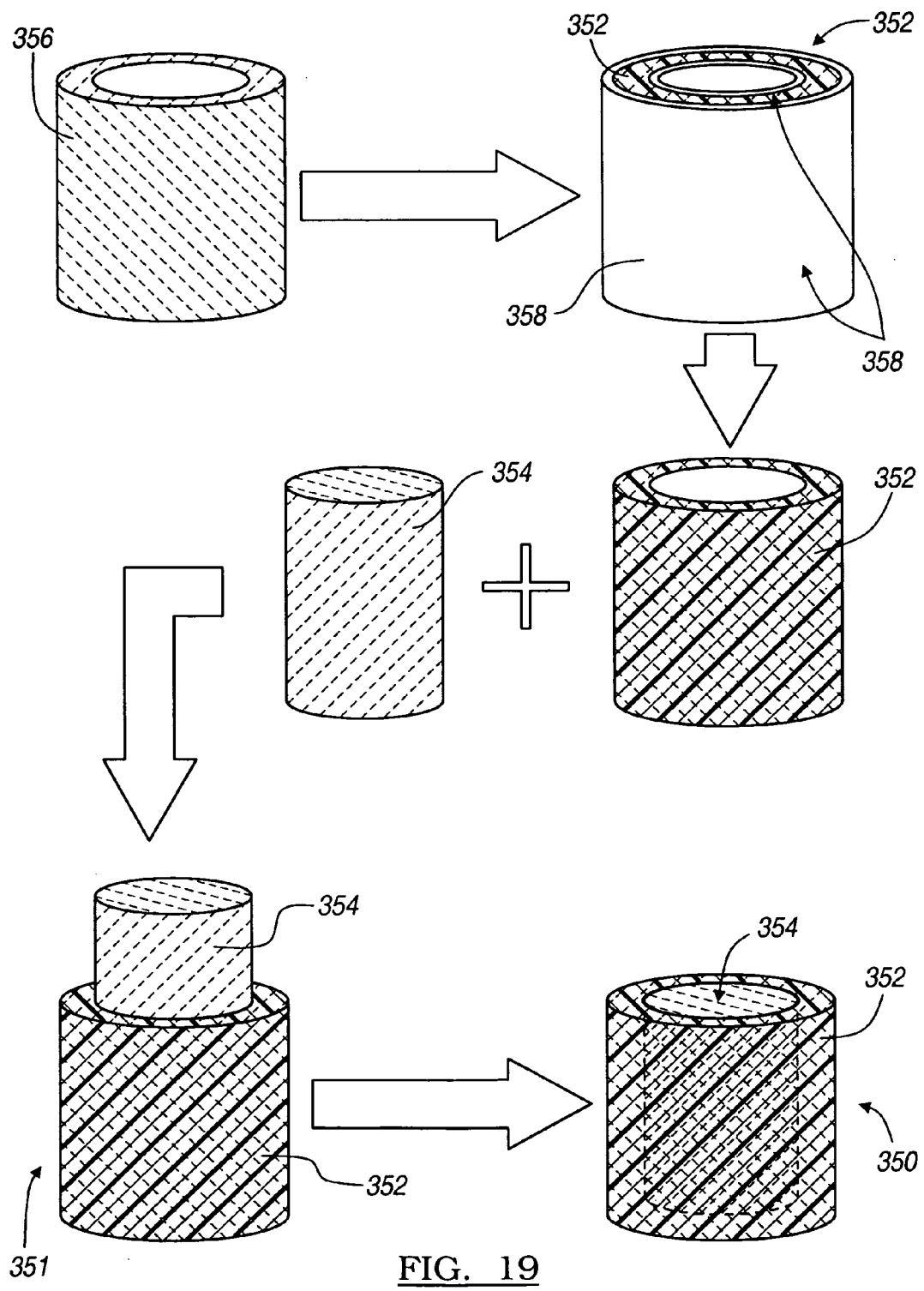
FIG. 19 is a flow chart of a method of forming an implant according to various embodiments.

With reference to FIG. 19, an implant 350 may be formed according to the illustrated method 351. A blank 356 may be formed of the structure material 10. The structure material 10 may be any appropriate porous material, such as a polymer matrix, ceramic, or the like. The blank may also be shaped into any appropriate geometry, such as cylinder.

The blank 356 may then be injected with the polymer, as discussed above. This may create polymer potions 358 that extend from a composite 352, that may be similar to the composite 20. The injection may occur by melting the polymer and injecting it under pressure into the pores and/or channels defined by the blank 356. The composite 352 may then have the exterior polymer portions 358 removed to include substantially only the composite 352.

A fill material 354 may then be inserted into the composite form 352. The fill material 354 may be any appropriate material. For example the fill material 354 may be substantially similar to the material that formed the blank 356. The two portions, including the fill 354 and the composite 352 may then be heated to meld the two together to form the implant 350.

The implant 350 may be similar to the implant 250 that included the graft material. In the implant 350, however, the fill material 354 may be formed into the implant and provided complete for a procedure. Thus, implants may be formed to include voids or pre-filled voids. The fill material 354 may serve the same purpose as the graft material discussed above, such as a void filling or support purposes. Nevertheless, the implant 350 may include the fill material 354 and be manufactured with the fill material 354.

Figure 20:
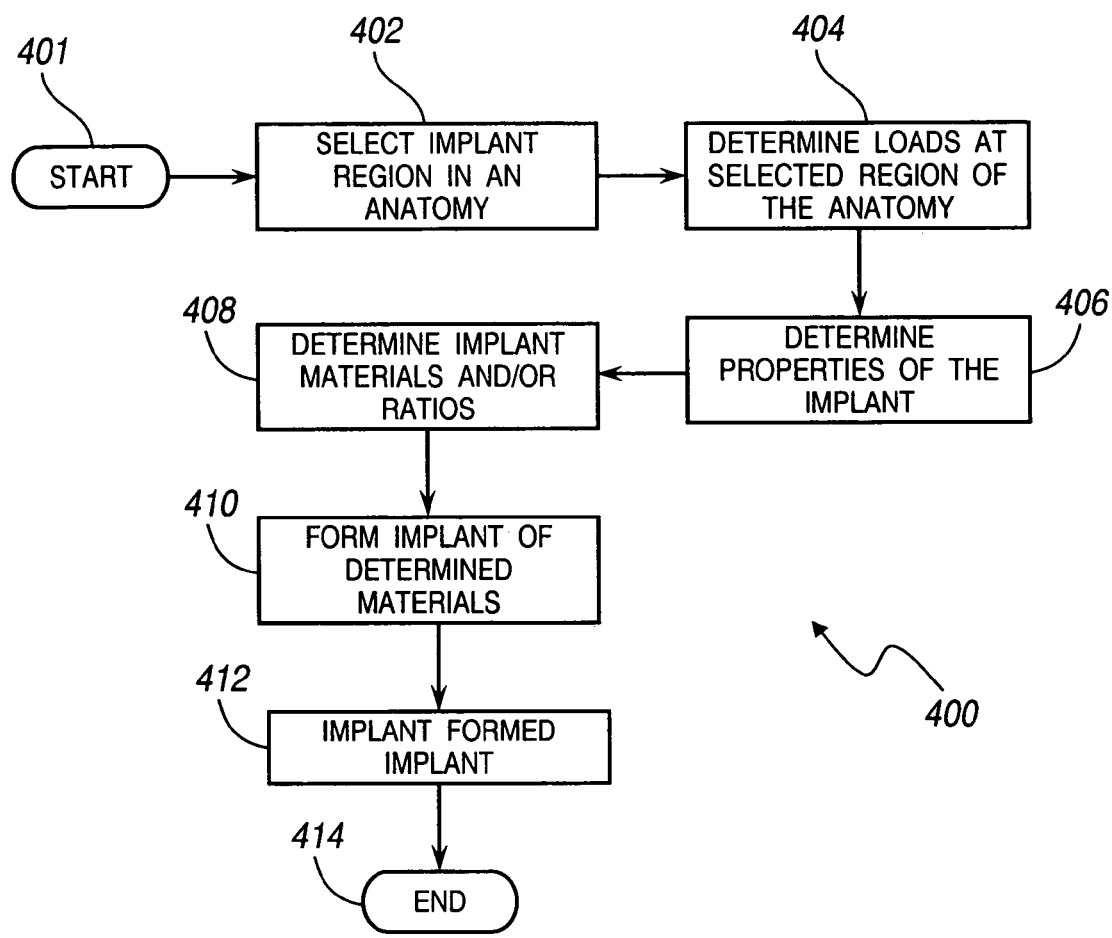
FIG. 20 is a flow chart of a method of forming an implant according to various embodiments.

With reference to FIG. 20 a flowchart 400 of a method of forming an implant according to various embodiments is illustrated. The method 400 may begin at a start block 401. Then a selected implant region is selected in block 402. The implant region may be any appropriate region of the anatomy. For example, a spinal region, a tibial region, a femoral region, a humeral region, or the like may be selected. As discussed above implants may be formed for any appropriate portion of the anatomy using the composite 20.

After the implant region is selected in block 402 loads may be determined relative to that that the region in block 404. For example, a compressive force, shear force, torsion force, or the like may be determined at the selected region of the anatomy. For example, it may be determined that about 1500-3000 N may be experienced in a spinal region. Although other forces may be determined and may depend upon a patient, the region selected, and other considerations.

Also other forces that the implant may experience can be determined. For example a torsion stress necessary for implantation may be determined. Thus not only forces in the selected region of the anatomy, but other forces may be determined in block 404. Properties of an implant may then be determined in block 406. For example, after the experienced forces are determined in block 404 the forces that the implant may be required to withstand, for various reasons, can be determined. For example, if the force experienced in the spine is about 1000 N it may be selected to form the implant to include a compressive strength of about 3000 N at about 6 months after implantation. Therefore, the loads determined in the anatomical region may be different than those determined as a property of the implant in block 406, but they may be related.

Also, a selected resorption time may be a property selected in block 406. For example, a resorption time of the implant may depend upon selected loads in the region of the anatomy or ingrowth rates at the selected regions, or other selected reasons. Thus the resorption time or profile of the implant may be determined in block 406. In this regard, bond ingrowth in various regions of the body may vary depending on the region, loads encountered, and anatomical condition of the area of interest.

Then implant materials may be determined in block 408. The materials selected may be the appropriate material to form the structure 10 or the appropriate polymer for the polymer fill 21. Although, as discussed above, both can be polymers or both can be ceramic materials. Also, the implant materials may be selected to achieve the selected properties, such as a strength, strength degradation profile, resorption profile, load bearing, etc. As also discussed above the materials selected may be a polymer of a selected molecular weight, a certain co-polymer, etc.

Also in determining the materials in block 408 the form of the implant can be determined when determining the implant materials in block 408, or at any appropriate time. As discussed above the implant may include a composite portion and a non-composite portion. Therefore, to achieve the determined properties of the implant, such designs may also be determined in block 408.

Then the implant can be formed in block 410. The implant may be formed of the materials determined in block 408 and the configuration determined in block 408. The implant may be formed according to any appropriate method and the formation method may also be chosen depending upon a selected property. For example, a polymer may be melted and then injected into a porous structure. Nevertheless, any appropriate method may be used to form the implant in block 410.

The implant formed in block 410 may then be implanted in block 412. As discussed above the implant may be customized by a user prior to implantation or it may be implanted as formed in block 410. Also a graft material may be used with the implant formed in block 410, also as discussed above. Generally, however, after the implant is formed in block 410 it can be implanted in block 412. Then generally the method ends in block 414.

The method 400, however, is merely exemplary and an implant may be formed of the composite 20 according to any appropriate method. The implant formed according to method 400 can include a selected property to achieve selected results after implantation. The selected properties can be achieved by selecting appropriate materials for the composite implant, a selected configuration of the implant, or other appropriate considerations.

Also, regardless of the method chosen the composite may be used to form an implant that includes a selected strength over a selected period of time, yet can still allow ingrowth of bone. The composite material may be formed into an implant where bone may grow into regions that are faster resorbing that other regions. This may be created by including the faster resorbing phase and the slower resorbing phase. The difference in resorption rates may be any appropriate difference, such as about 10% to about 200% different. Regardless, the slower resorbing phase may be selected for a strength quality to achieve a selected strength degradation profile, while the faster responding phase may be selected based upon the bone regrowth rate of the area of interest. This can assist in bone regrowth and in allowing recovery when a resorption may be selected in a load bearing area of the anatomy. This may also be used to achieve a selected strength of the implant for a selected period for any appropriate purpose.

As otherwise understood, the method 400 can be used to select materials and properties of the materials for a selected or unique application. The known or determine bone growth rate of a selected region of the anatomy can be used to assist in determining the materials to be used in forming the implant, the ratios of the materials to be used, or the specific properties of the materials to be used. Also the forces that are experienced in a selected region of the anatomy may be used to select the materials to be used to form an implant. Thus a higher selected strength may be used to select different materials for forming the implant. Therefore, the method 400 may be used to select materials for an implant, select a structure of an implant, or other features of the implant.

The teachings herein are merely exemplary in nature and, thus, variations that do not depart from the gist of the teachings are intended to be within the scope of the teachings. Such variations are not to be regarded as a departure from the spirit and scope of the teachings.

What is claimed is:

1. A resorbable spinal implant, comprising:
   a member including a composite formed of,
   a first material comprising a first resorbable material operable to be resorbed into an anatomy, the first material forming a scaffold having a plurality of pores and a plurality of continuous channels defined at least in part by a first sub-plurality of the plurality of pores, the plurality of channels extending through the scaffold; and
   a second material that is a resorbable polymer injected into the scaffold to substantially fill at least a sub-plurality of the plurality of continuous channels so that the polymer forms a continuous structure;
   wherein the second material is a polymer selected from the group comprising polylactic acids, polyglycolic acids, and combinations thereof, and forms about 55 wt % to about 65 wt % of the member;
   wherein the resorbable polymer is resorbed at a rate slower than a rate of resorption of the scaffold such that the resorbable polymer defines a support for bony ingrowth to maintain a selected strength of the member;
   wherein the member is operable to be positioned between a first vertebrae and a second vertebrae.

2. The implant of claim 1, wherein the second material is operable to resorb at a rate wherein the member remains substantially intact under at least about 2000 Newtons of compressive force after at least six months after implantation.

3. The implant of claim 1, wherein the member comprises a first wall having a height, a second wall having a height less than the height of the first wall, and a surface extending substantially orthogonal to and between the first wall and the second wall.

4. The implant of claim 3, wherein the member defines a void in the surface.

5. The implant of claim 3, wherein at least one continuous channel extends from the first wall to the second wall of the member.

6. The implant of claim 1, further comprising:
   a second sub-plurality of the plurality of pores that are only partially filled;
   wherein both the first sub-plurality of pores and the second sub-plurality of pores includes continuous pores with interconnecting channels.

7. The implant of claim 1, wherein the implant has a substantially linear rate of strength decrease over time;
   wherein rate of strength decrease of the implant is selected based upon the selected second material.

8. The implant of claim 1, wherein the first material comprises an absorbable ceramic.

* * * * *

UNITED STATES PATENT AND TRADEMARK OFFICE
CERTIFICATE OF CORRECTION

| | | |
|---|---|---|
| PATENT NO. | : 7,879,109 B2 | Page 1 of 1 |
| APPLICATION NO. | : 11/008075 | |
| DATED | : February 1, 2011 | |
| INVENTOR(S) | : Borden et al. | |

It is certified that error appears in the above-identified patent and that said Letters Patent is hereby corrected as shown below:

Col. 3, line 11: "illustrated in FIG. 1A" should be -- illustrated in FIG. 10A --

Signed and Sealed this
Twenty-fourth Day of January, 2012

David J. Kappos
*Director of the United States Patent and Trademark Office*